US010394008B2

(12) United States Patent
Bares et al.

(10) Patent No.: US 10,394,008 B2
(45) Date of Patent: Aug. 27, 2019

(54) HYPERSPECTRAL MULTIPHOTON MICROSCOPE FOR BIOMEDICAL APPLICATIONS

(71) Applicant: Cornell University, Ithaca, NY (US)

(72) Inventors: Amanda J. Bares, Ithaca, NY (US); Chris B. Schaffer, Ithaca, NY (US); Steven Tilley, Baltimore, MD (US)

(73) Assignee: Cornell University, Ithaca, NY (US)

(*) Notice: Subject to any disclaimer, the term of this patent is extended or adjusted under 35 U.S.C. 154(b) by 0 days.

(21) Appl. No.: 15/788,778

(22) Filed: Oct. 19, 2017

(65) Prior Publication Data

US 2018/0196246 A1 Jul. 12, 2018

Related U.S. Application Data

(60) Provisional application No. 62/410,345, filed on Oct. 19, 2016.

(51) Int. Cl.
*G01N 21/64* (2006.01)
*G02B 21/00* (2006.01)
(Continued)

(52) U.S. Cl.
CPC .......... *G02B 21/0064* (2013.01); *G01J 3/28* (2013.01); *G01J 3/4406* (2013.01);
(Continued)

(58) Field of Classification Search
CPC ....... G01N 21/6458; G01N 2021/6419; G01N 2021/6421; G01N 2021/6465;
(Continued)

(56) References Cited

U.S. PATENT DOCUMENTS 5,591,981 A * 1/1997 Heffelfinger .......... G01N 21/64
250/458.1
5,796,112 A 8/1998 Ichie
(Continued)

OTHER PUBLICATIONS

Nieman et al., "Hyperspectral imaging system for quantitative identification and discrimination of fluorescence labels in the presence of autofluorescence," 2006, 3rd IEEE international Symposium on Biomedical Imaging, pp. 1288-1291. (Year: 2006).*
(Continued)

*Primary Examiner* — Kiho Kim
(74) *Attorney, Agent, or Firm* — Perkins Coie LLP

(57) ABSTRACT

Optical sensing techniques and devices based on detection of fluorescent emissions at different optical wavelengths by nonlinear optical absorption of different excitation beams at different excitation wavelengths that interact with fluorescently-labeled structures within the sample to cause nonlinear optical absorption of two or more photons at each excitation wavelength. The fluorescent light at different fluorescent emission wavelengths by nonlinear optical absorption of excitation light at a particular excitation wavelength is spectrally separated into different optical channel output beams along different optical channel optical paths at different designated fluorescent imaging wavelength bands and the fluorescent light at different fluorescent imaging wavelengths within each designated fluorescent imaging wavelength is detected. This two-stage spectral separation in obtaining fluorescent images at different fluorescent imaging wavelengths in different fluorescent imaging wavelength bands enables highly sensitive hyperspectral imaging based on two-photo or multi-photon nonlinear absorption.

21 Claims, 14 Drawing Sheets

(51) Int. Cl.
G02B 26/00 (2006.01)
G01J 3/28 (2006.01)
G02B 21/16 (2006.01)
G01J 3/44 (2006.01)
G02B 27/14 (2006.01)
G02B 26/10 (2006.01)

(52) U.S. Cl.
CPC ....... *G01N 21/6458* (2013.01); *G02B 21/002* (2013.01); *G02B 21/0032* (2013.01); *G02B 21/0052* (2013.01); *G02B 21/16* (2013.01); *G02B 26/007* (2013.01); *G01N 2021/6419* (2013.01); *G01N 2021/6465* (2013.01); *G02B 21/0076* (2013.01); *G02B 26/105* (2013.01); *G02B 27/141* (2013.01); *G02B 2207/114* (2013.01)

(58) Field of Classification Search
CPC ............ G02B 21/0076; G02B 21/0064; G02B 21/002; G02B 21/0032; G02B 21/0052; G02B 21/16; G02B 26/007; G02B 26/105; G02B 27/141; G02B 2207/114; G01J 3/28; G01J 3/4406
See application file for complete search history.

(56) References Cited

U.S. PATENT DOCUMENTS

| | | | |
|---|---|---|---|
| 5,835,262 | A | 11/1998 | Iketaki et al. |
| 5,836,877 | A | 11/1998 | Zavislan |
| 6,094,300 | A | 7/2000 | Kashima et al. |
| 6,169,289 | B1 | 1/2001 | White et al. |
| 6,403,332 | B1 | 6/2002 | Bearman et al. |
| 6,750,036 | B2 | 6/2004 | Bearman et al. |
| 6,818,903 | B2 | 11/2004 | Schomacker et al. |
| 6,839,661 | B2 | 1/2005 | Costa et al. |
| 6,933,154 | B2 | 8/2005 | Schomacker et al. |
| 7,005,654 | B2 | 2/2006 | Seyfried |
| 7,420,678 | B2 | 9/2008 | Lundgren et al. |
| 7,507,582 | B2 | 3/2009 | Heinze et al. |
| 7,668,586 | B2 | 2/2010 | Hyman et al. |
| 7,943,909 | B2 * | 5/2011 | Mano ................. G01N 21/6458 250/226 |
| 8,094,304 | B2 | 1/2012 | Raicu et al. |
| 8,385,615 | B2 | 2/2013 | Levenson et al. |
| 8,982,206 | B2 | 3/2015 | Raicu et al. |
| 9,568,418 | B1 * | 2/2017 | Hug ........................... G01J 3/10 |
| 2003/0222222 | A1 * | 12/2003 | Dong ................. G01N 21/6428 250/458.1 |
| 2004/0196457 | A1 * | 10/2004 | Aono ................. G01N 21/6458 356/318 |
| 2004/0217256 | A1 * | 11/2004 | Ortyn ................. G01N 15/1459 250/201.4 |
| 2006/0237666 | A1 * | 10/2006 | Kubo ........................ G01J 3/10 250/458.1 |
| 2007/0147673 | A1 * | 6/2007 | Crandall .............. G02B 21/367 382/128 |
| 2009/0116008 | A1 * | 5/2009 | Fukuda .............. G01N 21/6428 356/317 |
| 2009/0173892 | A1 * | 7/2009 | Courtney ........... G01N 21/6408 250/484.4 |
| 2011/0134516 | A1 * | 6/2011 | Araya ................ G02B 21/0004 359/371 |
| 2011/0278470 | A1 * | 11/2011 | Bouzid ...................... G01J 1/58 250/459.1 |
| 2013/0236061 | A1 * | 9/2013 | Suzuki ............... G01N 21/6458 382/103 |

OTHER PUBLICATIONS

Favreau, P.F. et al., "Tunable thin-film optical filters for hyperspectral microscopy," presented at the SPIE BiOS, 2013, vol. 8589, pp. 85890R-85890R-5.

Leavesley, S.J. et al., "Hyperspectral imaging microscopy for identification and quantitative analysis of fluorescently-labeled cells in highly autofluorescent tissue," J. Biophoton., 2011, vol. 5, No. 1, pp. 67-84.

Livet, J. et al., "Transgenic strategies for combinatorial expression of fluorescent proteins in the nervous system.," Nature, 2007, vol. 450, No. 7166, pp. 56-62.

Mahou et al., "Multicolor two-photon tissue imaging by wavelength mixing," Nat. Methods, 2012, vol. 9, No. 8, pp. 815-818.

Misgeld et al., "In vivo imaging of the diseased nervous system," Nature Reviews Neuroscience, 2006, vol. 7, No. 6, pp. 449-463.

Nshimura et al., "Big Effects From Tiny Vessels: Imaging the Impact of Microvascular Clots and Hemorrhages on the Brain," Stroke, 2013, vol. 44, No. 6, pp. S90-S92.

Radosevich et al., "Hyperspectral in vivo two-photon microscopy of intrinsic contrast," Optics Letters, 2008, vol. 33, No. 18, pp. 2164-2166.

Sturzl et al., "Novel Micro-Raman Setup with Tunable Laser Excitation for Time-Efficient Resonance Raman Microscopy and Imaging," Analytical Chemistry, 2013, 85, pp. 4554-4559.

Zimmermann, T. et al., "Spectral imaging and its applications in live cell microscopy," FEBS Letters, 2003, vol. 546, No. 1, pp. 87-92.

* cited by examiner

HYPERSPECTRAL MULTIPHOTON MICROSCOPE FOR BIOMEDICAL APPLICATIONS

PRIORITY CLAIMS AND RELATED PATENT APPLICATIONS

This patent document claims the priority and benefits of U.S. Provisional Application No. 62/410,345 entitled "HYPERSPECTRAL MULTIPHOTON MICROSCOPE FOR BIOMEDICAL APPLICATIONS" and filed on Oct. 19, 2016. The entirety of the above application is incorporated by reference as part of the disclosure of this patent document.

TECHNICAL FIELD

This patent document relates to biomedical sensing and imaging based on nonlinear optical absorption in fluorescently-tagged structures.

BACKGROUND

A multiphoton microscopy such as two-photon excitation fluorescence (2PEF) microscopy is a fluorescence imaging technique that is based on nonlinear optical absorption in fluorescently-tagged structures and is useful for visualizing fluorescently-tagged cells in living animal tissue. The nonlinear excitation involves absorption of two or more excitation photons to excite a single fluorescent molecule from a low energy ground state to a higher energy state. Once the fluorophore is in an excited state, the fluorophore decays to the ground energy state to release energy in the form of single-photon fluorescence. In two-photon absorption, the fluorescence signal intensity scales as the square of the laser excitation intensity and a high photon flux in a volume is required. The 2PEF technique can be used to overcome tissue scattering through inherent optical sectioning by generating in-focus images of a plane in a three-dimensional (3D) sample, without requiring physical sectioning of the sample. In wide-field fluorescence microscopy, the entire field of view (FOV) is illuminated by an ultraviolet (UV) source which generates fluorescence throughout the sample. The sample is "imaged" with a microscope objective that replicates the image on a viewer's retina or a camera. If the sample is too thick (i.e. more than a few cells thick), fluorescence is generated everywhere structures are labeled, and an acquired image may contain signals from tagged structures at varying depths to appear as a blurry image.

2PEF provides optical sectioning through nonlinear excitation of fluorophores which tends to occur in the small, sub-micrometer focus of the microscope objective. Because out-of-plane fluorescence is not generated in the first place, detected photons are mostly attributed to the current location of the focal volume. This optical sectioning in 2PEF can be paired with a line-scanning microscope to generate 3D images of fluorescent structures.

SUMMARY

This patent document discloses optical sensing techniques and devices based on detection of fluorescent emissions at different optical wavelengths by nonlinear optical absorption of different excitation beams at different excitation wavelengths that interact with fluorescently-labeled structures within the sample to cause nonlinear optical absorption of two or more photons at each excitation wavelength. The fluorescent light at different fluorescent emission wavelengths by nonlinear optical absorption of excitation light at a particular excitation wavelength is spectrally separated into different optical channel output beams along different optical channel optical paths at different designated fluorescent imaging wavelength bands and the fluorescent light at different fluorescent imaging wavelengths within each designated fluorescent imaging wavelength is detected. This two-stage spectral separation in obtaining fluorescent images at different fluorescent imaging wavelengths in different fluorescent imaging wavelength bands enables highly sensitive hyperspectral imaging based on two-photo or multi-photon nonlinear absorption.

In one aspect, a multiphoton microscope is provided to include a sample stage, a light source, a microscope objective, an optical output device, optical channel detectors, and tunable optical channel filters. The sample stage holds a sample to be imaged. The light source (or multiple sources) can be used to generate different excitation beams at different excitation wavelengths that interact with fluorescently-labeled structures within the sample to cause nonlinear optical absorption of two or more photons at each excitation wavelength and leading to fluorescent emission of light at one or more fluorescent emission wavelengths different from the corresponding excitation wavelength. The optical input device is located in optical paths of the excitation beams between the light source and the sample stage and is structured to direct the excitation beams to the sample stage. The microscope objective is located in the optical paths of the excitation beams between the optical input device and the sample stage to direct the excitation beams toward the sample stage to illuminate the sample and to collect light from the sample. The optical output device is located relative to the microscope objective to receive collected light by the microscope objective from the sample and selects emitted light at the fluorescent emission wavelengths as an output beam while excluding from the output beam light at each excitation wavelength. The optical output device includes wavelength-selective optical devices that separate the output beam into different optical channel output beams along different optical channel optical paths at different designated fluorescent imaging wavelength bands, respectively, one optical channel output beam from one wavelength-selective optical device. The optical channel detectors are located along the different optical channel optical paths to receive the different optical channel output beams, respectively, so that each optical channel detector receives a corresponding optical channel output beam and produces an optical channel detector output having information of the sample at within a corresponding fluorescent imaging wavelength band for the corresponding optical channel output beam. The tunable optical channel filters are located between the optical channel detectors and wavelength-selective optical devices in the different optical channel optical paths, respectively, to receive the different optical channel output beams at the different designated fluorescent imaging wavelength bands, each tunable optical channel filter operable to spectrally tune and select light at different optical imaging wavelengths within a corresponding designated fluorescent imaging wavelength band to be present in a corresponding optical channel output beam to be received by a corresponding optical channel detector, wherein each optical channel output beam from an optical channel detector contains imaging information at the different optical imaging wavelengths within a corresponding designated fluorescent imaging wavelength band and the different optical channel output beams contain imaging information at the different optical imaging wavelengths in the designated fluorescent imaging wavelength bands.

In another aspect, a method of microscopy based on multiphoton excitation is provided to include selecting different excitation laser wavelengths of excitation light for multiphoton excitation with respect to certain fluorescent labeling tags used in a sample, and sequentially directing excitation laser beams at the different selected excitation laser wavelengths to the sample to cause emission of fluorescent light in a florescent spectrum due to nonlinear multiphoton excitation at each excitation laser wavelengths. The method also includes collecting the fluorescent light emitted from the sample at a corresponding fluorescent spectrum associated with each of the different excitation laser wavelengths, and dividing collected light in each fluorescent spectrum into different broad color channels. The method further includes selecting light at different imaging wavelengths within each broad color channel to be imaged to obtain images at different fluorescent imaging wavelengths within each and all broad color channels, and processing obtained images at different fluorescent imaging wavelengths within each and all broad color channels to extract information on the sample.

In another aspect, a method of imaging a sample based on nonlinear optical absorption and fluorescent emission in the sample includes directing to a sample different excitation beams at different excitation wavelengths that interact with the sample to cause nonlinear optical absorption of two or more photos at each excitation wavelength to emit light at one or more fluorescent emission wavelengths different from the corresponding excitation wavelength. The method also includes operating a microscope objective to direct the excitation beams toward the sample to illuminate the sample and to collect light from the sample. The collected light at the microscope objective includes returned excitation light at the excitation wavelengths and emitted light via nonlinear optical absorption at fluorescent emission wavelengths. The method includes selecting from the collected light by the microscope objective from the sample the emitted fluorescent light at the fluorescent emission wavelengths by the sample as an output beam, and separating the output beam into different optical channel output beams along different optical channel optical paths at different designated fluorescent imaging wavelength bands, respectively. The method also includes operating different optical channel filters in the different optical channel optical paths, respectively, to receive and filter the different optical channel output beams at the different designated fluorescent imaging wavelength bands so that each optical channel filter selects light at different fluorescent imaging wavelengths within a corresponding designated fluorescent imaging wavelength band to be in a corresponding optical channel output beam while collecting all available light at each fluorescent imaging wavelength within a corresponding designated fluorescent imaging wavelength band in the corresponding optical channel output beam without using an optically dispersive element to spatially separate light at different fluorescent imaging wavelengths within each corresponding designated fluorescent imaging wavelength band, and operating different optical channel detectors located along the different optical channel optical paths to receive the different optical channel output beams, respectively, so that each optical channel detector receives a corresponding optical channel output beam at the different fluorescent imaging wavelengths for each and all designated fluorescent imaging wavelength bands and produces optical channel detector outputs having information of the sample at the different fluorescent imaging wavelengths for each and all designated fluorescent imaging wavelength bands.

The above and other aspects and features, and exemplary implementations and applications, are described in greater detail in drawings, the description and the claims.

DETAILED DESCRIPTION

Figure 1:
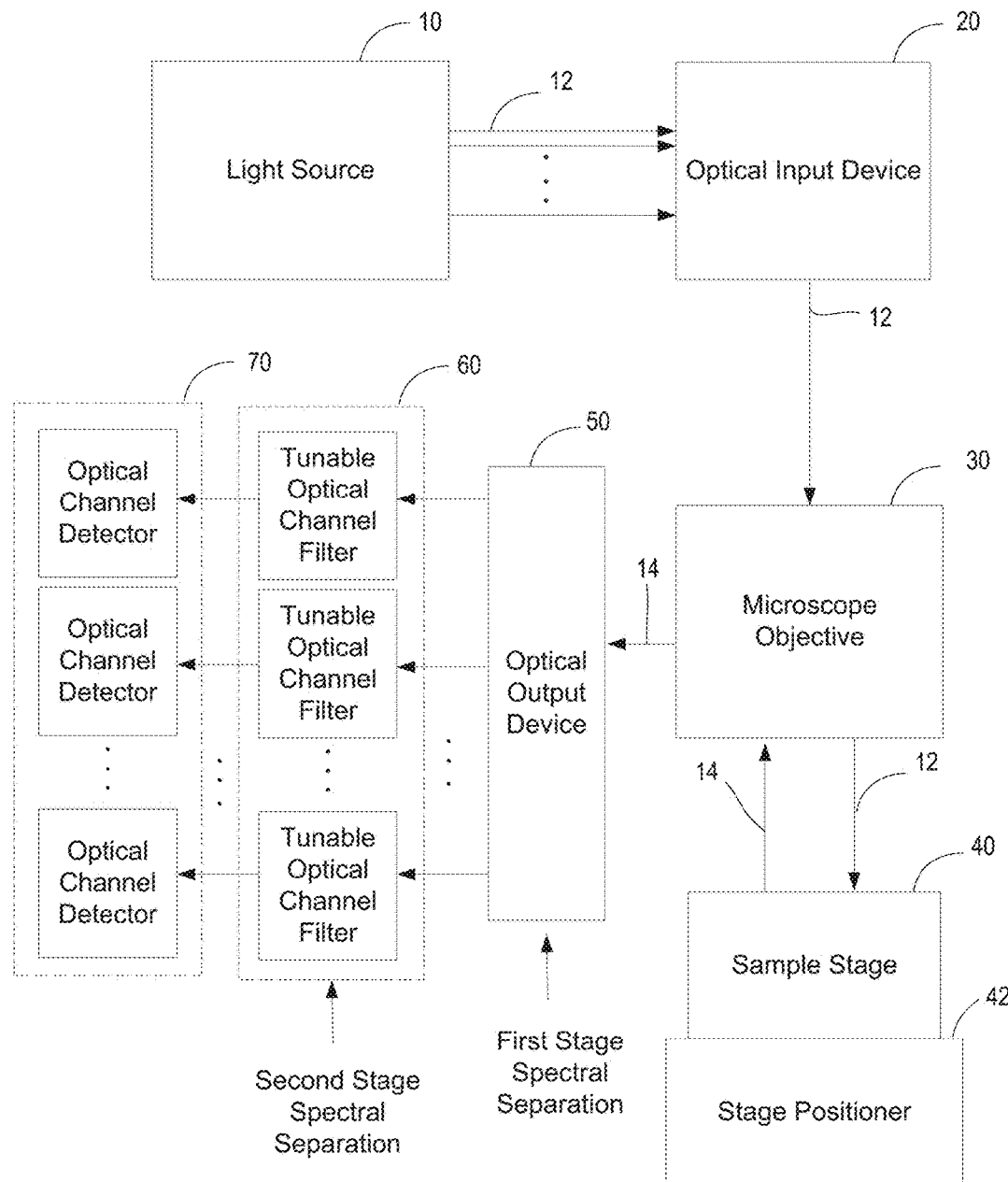
FIG. 1 illustrates an example configuration of a hyperspectral multiphoton microscope.

The techniques and devices disclosed in this document provide a hyperspectral multiphoton microscope for imaging of multiple, overlapping fluorescent labels for biomedical applications such as multicellular studies.

One significant limitation for visualizing multiple cells and cell types, all tagged with unique fluorescent label colors, is the lack of spectral resolution in most nonlinear microscope instrument designs, which typically incorporate just 2-4 different wavelength detection channels. Some existing instrument designs incorporate dispersive optical elements (e.g., prisms, gratings) to provide improved spectral resolution. However, when imaging deep in tissue, these spectral advantages disappear due to scattering effects, leading to loss of spectral resolution at depth.

The multiphoton microscopy can be used to directly observe and quantify the behavior of, and interactions between, cells in living organisms. This has been used primarily as a tool for hypothesis testing, where cell types of interest are labeled using genetic strategies or exogenous dyes and are imaged on microscopes that feature 2-4 simultaneous fluorescence detection channels. In these kinds of experiments, "red" and "green" labeled cells (or other structures) stand out against a black background. That black space is not empty, however, but is densely filled with other cell types that are not seen and whose role, therefore, cannot be examined. In addition, autofluorescence generated by endogenous fluorescent species often has a broad fluorescent emission spectrum, leading to the inability to separate this signal from exogenous fluorescent labels. Modern genetic labeling strategies, such as the various Brainbow constructs, are approaching the point where every cell in a volume can be labeled with a unique combination of fluorescent proteins. Clearly differentiating these color combinations and thus delineating the cells, however, requires much more information than can be acquired on current microscopes that image well in vivo. Use of these powerful labeling strategies has thus been limited primarily to post-mortem imaging of tissue using confocal microscopes, which are too sensitive to optical scattering for robust in vivo use.

Some existing nonlinear microscopes utilize an optical dispersing element such as a grating or prism to spatially separate different spectral components in collected fluorescent light onto a spatially resolved detector, e.g., by translating the fluorescent emission spectrum onto different locations on a photodetector array such as a photomultiplier tube array. This spatial separation of different spectral components in the fluorescent light can causes spectral blurring if divergent rays from the sample are routed into the detection system (such as when large area optics are used to capture scattered light), leading to a general loss of spectral resolution as a function of imaging depth. This limits the utility of these systems in scattering samples, such as live animals. Alternatively, signal from different labels can be distinguished based on the wavelength dependence of the two-photon excitation cross section. Using fixed wavelength detection channels, collected images at multiple excitation wavelengths between 710 and 920 nm quantify the relative abundance of autofluorescent species in tissue samples. A single-source excitation from a Ti:Sapphire laser and an optical parametric oscillator may be used together with nondegenerate two-color excitation from both beams to independently excite and detect three fluorophores with distinct two-photon absorption spectra.

The hyperspectral multiphoton microscope technique can be used to provide superior imaging capabilities based on two-photon excitation of fluorescent molecules for image contrast to significantly expand the amount of spectral information in imaging scattering tissue, such as in animal models. In implementations, large area optics can be used to collect a divergent cone of light exiting from the back aperture of the microscope objective, retaining the signal from scattered photons from deep in the sample. This allows imaging at greater depths in scattering tissues (i.e., mouse cortex).

The hyperspectral multiphoton microscope disclosed in this document utilizes two-stage spectral separation to first separate the collected fluorescent light from the sample into different optical channel output beams along different optical channel optical paths at different designated fluorescent imaging wavelength bands, and, subsequently, within each optical channel output, further use a tunable optical filter (such as an angle-tunable bandpass filter with a high transmission efficiency) to select different optical imaging wavelengths within a designated fluorescent imaging wavelength band to be detected by a photodetector. The optical design for using a tunable optical filter to select different optical imaging wavelengths within a designated fluorescent imaging wavelength band eliminates the need for spatially separating different spectral components for optical detection and thus reduces the spectral blurring. A collimating optical design for each detection channel allows for collection of fluorescent emission light at diverging angles to improve detection sensitivity, leads to minimal spectral blurring and high signal-to-noise ratio as a function of imaging depth, and provides the capability for high spatial resolution (~0.5 μm). The two-stage spectral separation based on the disclosed technology may be implemented in various configurations by using a sample stage that holds a sample to be imaged that contains fluorescently-labeled structures and a light source (a single light source or multiple light sources) that generates different excitation beams at different excitation wavelengths that interact with fluorescently-labeled structures within the sample to cause nonlinear optical absorption of two or more photons at each excitation wavelength and leading to fluorescent emission of light at one or more fluorescent emission wavelengths different from the corresponding excitation wavelength. A microscope objective can be placed in an optical path of the excitation beams relative to the sample stage to direct the excitation light to illuminate the sample to induce the nonlinear optical absorption and to collect light from the sample for the imaging operation.

An optical input device can be located in an optical path between the light source and the sample stage to direct the excitation light of the excitation beams at different excitation wavelengths to the microscope objective which further directs the excitation light to the sample on the sample stage. The optical input device may include beam directing optics for directing the excitation beams and may also include a beam scanning device for scanning the excitation light to different locations on the sample for point scanning or for imaging different parts of the sample. In some implementations, the sample stage may include or be engaged to a positioning device or translational actuator that can translate the position of the sample relative to the excitation light to allow imaging different parts of the sample. In some implementations, both translation in position of the sample stage and the scanning of the excitation light may be used in combination to direct the excitation light to image different parts of the sample.

The two-stage spectral separation can be implemented as the follows. For detecting the collected light from the sample by the microscope objective, an optical output device is placed or located relative to the microscope objective to receive collected light by the microscope objective from the sample and select emitted light at the fluorescent emission wavelengths as an output beam while excluding from the output beam light at each excitation wavelength. The optical output device is structured to also separate the output beam into different optical channel output beams along different optical channel optical paths at different designated fluorescent imaging wavelength bands, respectively. This is the first stage spectral separation for the hyperspectral imaging. The optical output device may, in some implementations, include wavelength-selective optical devices to separate the output beam into the different optical channel output beams, respectively, so that one wavelength-selective optical device operates to produce one optical channel output beam. Such a wavelength-selective optical device may be implemented in various configurations, including, e.g., dichroic optical elements such as dichroic beam splitters.

To detect the different optical channel output beams for hyperspectral imaging, optical channel detectors are located along the different optical channel optical paths to receive the different optical channel output beams, respectively, so that each optical channel detector receives a corresponding optical channel output beam and produces an optical channel detector output having information of the sample at within a corresponding fluorescent imaging wavelength band for the corresponding optical channel output beam.

Notably, the second stage spectral separation for the two-stage spectral separation is implemented by placing tunable optical channel filters located between the optical channel detectors and wavelength-selective optical devices in the different optical channel optical paths, respectively. The tunable optical channel filters receive the different optical channel output beams at the different designated fluorescent imaging wavelength bands. Each tunable optical channel filter is operable to spectrally tune and select light at different optical imaging wavelengths within a corresponding designated fluorescent imaging wavelength band to be present in a corresponding optical channel output beam for detection by a corresponding optical channel detector. This second stage spectral separation increases the number of the different fluorescent imaging wavelengths for capturing two-photon fluorescent images of the sample while allowing the maximum amount of the fluorescent light at each fluorescent imaging wavelength to be captured because the use of the second stage spectral separation is based on spectral filtering using an optical passband filter without using an optically dispersive element for spatially separating different spectral components in the collected light. Under this two-stage spectral separation design, each optical channel output beam from an optical channel detector contains imaging information at the different optical imaging wavelengths within a corresponding designated fluorescent imaging wavelength band and the different optical channel output beams contain imaging information at the different optical imaging wavelengths in the designated fluorescent imaging wavelength bands. In this regard, assuming, there are M designated fluorescent imaging wavelength bands produced by the wavelength-selective optical devices in the optical output device and N different optical imaging wavelengths produced by each tunable optical filter within a corresponding designated fluorescent imaging wavelength band, the total number of different optical imaging wavelength bands is (M×N).

In some implementations, a hyperspectral multiphoton microscope can be implemented based on the above two-stage spectral separation to include multiple excitation lasers and a custom, angle-tunable bandpass filter approach to maintain imaging depth and high spectral resolution simultaneously.

FIG. 1 illustrates an example of the microscope having a light source 10, an optical input device 20, a microscope objective 30, a sample stage 40, a stage positioner 42, an optical output device 50, tunable optical channel filters 60, and optical channel detectors 70. The sample stage 40 holds a sample to be imaged. The light source 10 generates different excitation beams 12 at different excitation wavelengths. The light source 10 include different lasers for producing the different excitation beams at the different excitation wavelengths. In some implementations, such different lasers may be controlled to turn on sequentially, with one laser at a time, to interact with the sample to cause nonlinear optical absorption of two or more photons at each excitation wavelength to emit light at one or more fluorescent emission wavelengths different from the corresponding excitation wavelength. The optical input device 20 is located in optical paths of the excitation beams 12 between the light source 10 and the sample stage 40 and is structured to direct the excitation beams 12 to the sample stage 40. The microscope objective 30 is located in optical paths of the excitation beams 12 between the optical input device 20 and the sample stage 40 to direct the excitation beams 12 toward the sample stage 40 to illuminate the sample and to collect light from the sample. The optical output device 50 is located relative to the microscope objective 30 to receive collected light 14 by the microscope objective 30 from the sample and select emitted light at the fluorescent emission wavelengths as an output beam while excluding from the output beam light at the excitation wavelengths. The optical output device 50 includes wavelength-selective optical devices (not illustrated in FIG. 1) as the first stage spectral separation to separate the output into different optical channel output beams along different optical channel optical paths at different designated fluorescent imaging wavelength bands, respectively, one optical channel output beam from one wavelength-selective optical device. The optical channel detectors 70 are located along the different optical channel optical paths to receive the different optical channel output beams, respectively, so that each optical channel detector 70 receives a corresponding optical channel output beam and produces an optical channel detector output having information of the sample at within a corresponding fluorescent imaging wavelength band for the corresponding optical channel output beam. The tunable optical channel filters 60 are provided as the second stage spectral separation between the optical channel detectors 70 and wavelength-selective optical devices in the different optical channel optical paths, respectively, to receive the different optical channel output beams at the different designated fluorescent imaging wavelength bands. Each tunable optical channel filter 60 is operable to spectrally tune and select light at different optical imaging wavelengths within a corresponding designated fluorescent imaging wavelength band to be present in a corresponding optical channel output beam to be received by a corresponding optical channel detector. Each optical channel output beam from an optical channel detector 70 contains imaging information at the different optical imaging wavelengths within a corresponding designated fluorescent imaging wavelength band and the different optical channel output beams contain imaging information at the different optical imaging wavelengths in the designated fluorescent imaging wavelength bands.

The light source 10 may generate a number of individual laser beams tuned to separate wavelengths. Each laser beam may be tuned to a different wavelength longer than 650 nm. For example, the light source 10 may utilize a tightly-focused, infrared wavelength (700-1,300 nm), femtosecond duration pulsed laser source. In an implementation, the light source 10 generates a number of laser beams simultaneously. The laser beams are directed to the sample stage 40 through the microscope objective 30. In another implementation, the light source 10 produces a laser beam that incrementally or decrementally adjusts its wavelength. In the implementation where the light source 10 generates a number of laser beams simultaneously, the wavelengths of the number of laser beams may be incrementally or decrementally adjusted. The number of laser beams are chosen to variably excite selected fluorescent labels in the sample 40. For example, the light source 10 may generate three laser beams having wavelengths of 800 nm, 920 nm, and 1045 nm, respectively. Alternatively, the light source 10 may generate three lasers having wavelengths of 800 nm, 900 nm, and 1030 nm, respectively. The laser beams or the combined laser beam may be routed onto a scan mirror or a set of scan mirrors (e.g., galvanometer or resonant) and sent through a scan and tube lens so the scan mirrors are imaged onto the back aperture of the microscope objective 30. The optical input device 20 is placed before the microscope objective 30 to direct the laser beams to the microscope objective 30. In some implementations, the optical input device 20 may include one or more dichroic mirrors that allow the laser beam to pass therethrough or to be deflected. For example, the optical input device 20 may include a dichroic mirror with a cutoff wavelength greater than the fluorescent imaging wavelength band but smaller than the excitation band.

The sample is placed on the sample stage 40, immediately beneath the microscope objective 30. The sample stage 40 may be placed on the stage positioner 42 such as a motorized stage positioner. The light 14 emitted from the sample is collected in the microscope objective 30 and sent to the optical output device 50. In some implementations, the optical input device may further include a lens system (not illustrated) placed before the microscope objective 30 translates an angle of the laser beam into a position in the field of view of the microscope objective. The lens system may include scan and tube lenses.

Figure 2:
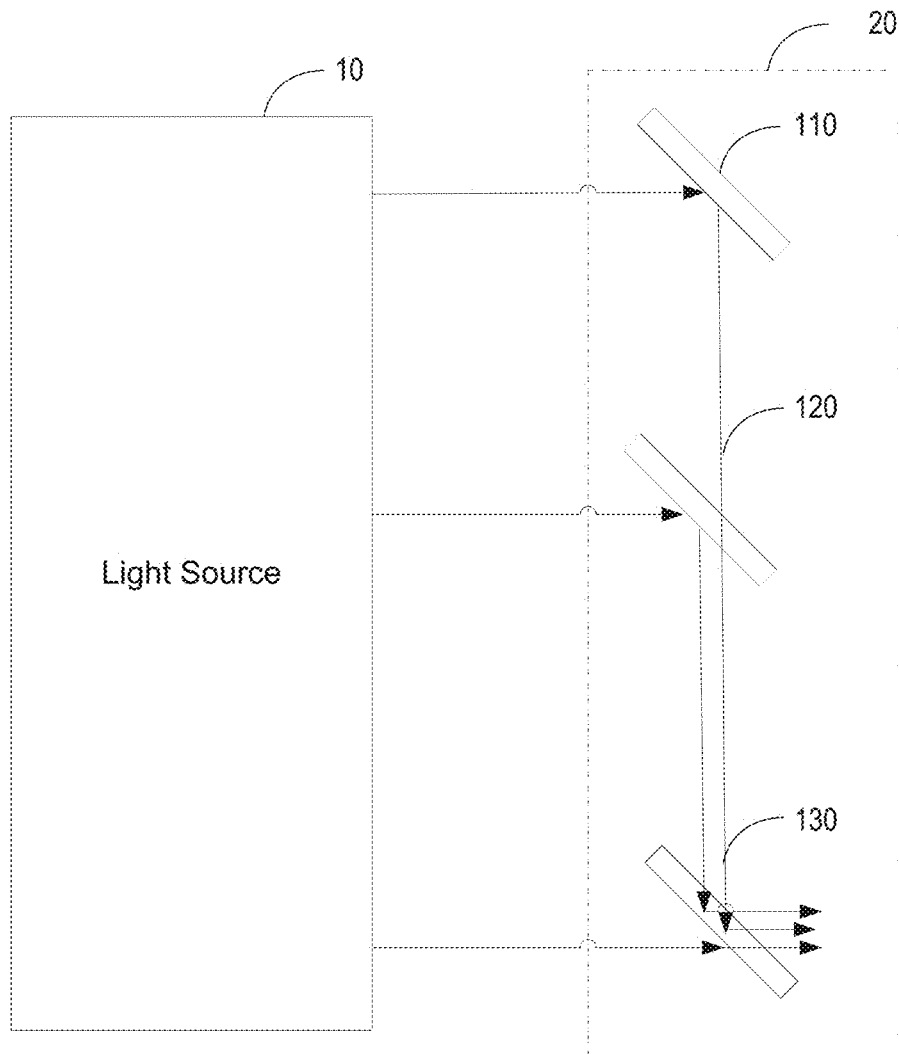
FIG. 2 illustrates an example of an optical input device.

FIG. 2 illustrates an example of the optical input device 20. In an implementation where the light source 10 generates a number of laser beams simultaneously, the optical input device 20 may combine multiple laser beams to direct the combined laser beam to the sample stage 40. In this implementation, the optical input device 20 includes a mirror 110 and a combination of first and second dichroic mirrors 120 and 130. The mirror 110 deflects light to redirect the light to the dichroic mirrors 120 and 130. For example, in an implementation where the light source 10 generates three lasers having wavelengths of 800 nm, 920 nm, and 1045 nm, respectively, the mirror 110 redirects the 920 nm laser. The first dichroic mirror 120 allows the 920 nm laser to pass therethrough and deflects the 1045 nm laser toward the second dichroic mirror 130. The second dichroic mirror 130 allows the 800 nm laser to pass therethrough and deflects the 920 nm and 1045 nm lasers so that all the three lasers travel in the same direction.

Figure 3:
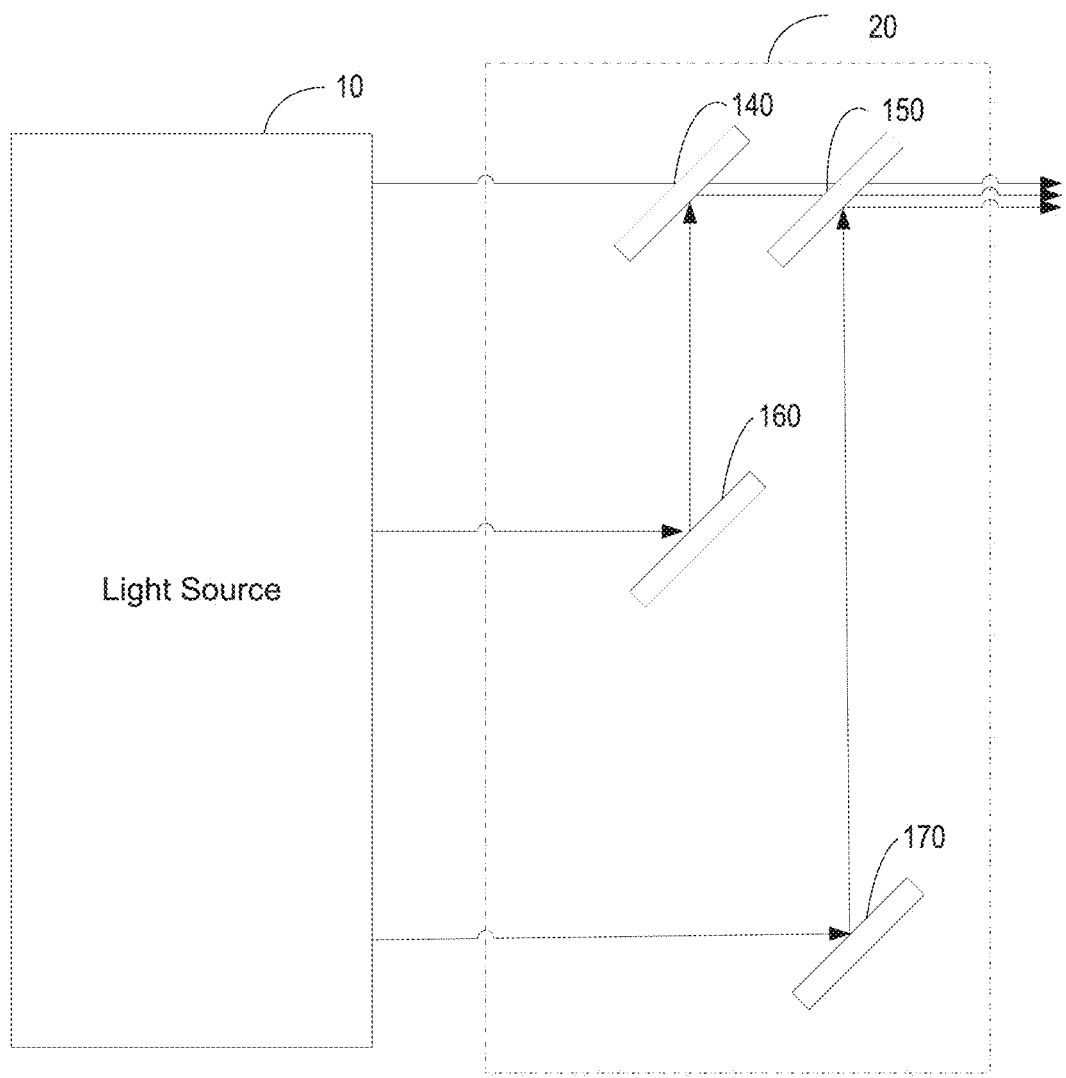
FIG. 3 illustrates another example of the optical input device.
Figure 4:
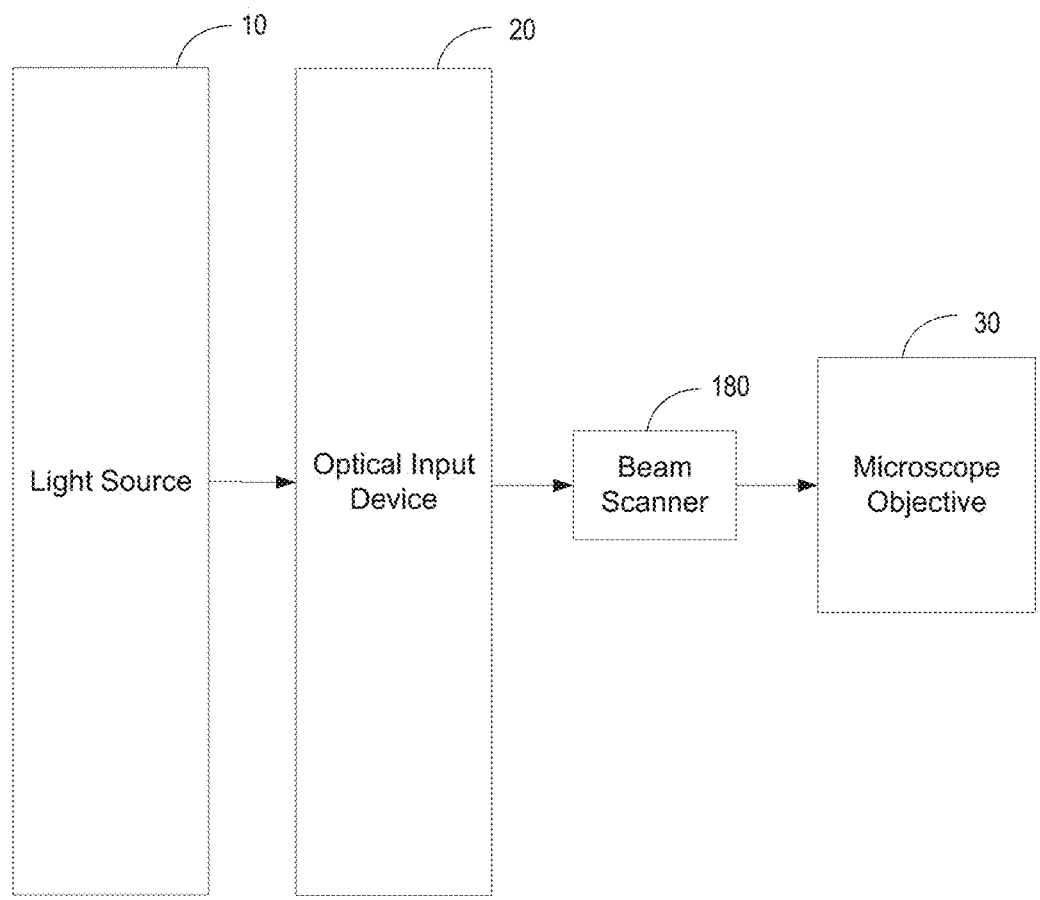
FIG. 4 illustrates an example of the hyperspectral multiphoton microscope having a beam scanner between an optical input device and a microscope objective.

FIG. 3 illustrates another example of the optical input device 20. In the implementation where the light source 10 generates a number of laser beams simultaneously, the optical input device 20 may combine multiple laser beams to direct the combined laser beam to the sample stage 40 by using two mirrors 160 and 170 and a combination of short pass and long pass dichroic mirrors 140 and 150. For example, in an implementation where the light source 10 generates three lasers having wavelengths of 800 nm, 900 nm, and 1030 nm, respectively, the mirror 160 and 170 redirects the 1030 nm and the 800 nm lasers toward the short pass and long pass dichroic mirrors 140 and 150, respectively. The short pass dichroic mirror 140 allows the 900 nm laser to pass therethrough and deflects the 1030 nm laser toward the long pass dichroic mirror 150. The long pass dichroic mirror 150 allows the 900 nm and the 1030 nm lasers to pass therethrough and deflects the 800 nm laser so that all the three lasers travel in the same direction.

FIG. 3 illustrates an example of the hyperspectral multiphoton microscope having a beam scanner 180 between the optical input device 20 and the microscope objective 30. The beam scanner 180 may include a controllable structure that deflects light and allows the light to be redirected for scanning of the sample by the laser beam. The beam scanner 180 may a scan mirror that includes galvanometer or resonant. If the light source 10 generates one or more femtosecond pulsed laser beams tuned to different wavelengths such as different infrared wavelength, each laser beam is expanded to a size that will overfill the back aperture of the microscope objective 30 to provide optimal resolution. In some implementations, a power control system and shutter (not illustrated) may be placed into each laser beam path, such as an electronic shutter, half waveplate and polarizing beam splitter cube, to enable the power of each laser beam to be adjusted and to control when each laser beam irradiates the sample.

As the laser beam (e.g., the tightly-focused, infrared wavelength, femtosecond duration pulsed laser) is applied to the sample 40, a nonlinear excitation of fluorescent markers occurs. The hyperspectral multiphoton microscope disclosed in this document relies on two-photon excitation of fluorescent molecules for image contrast, but can significantly expand the amount of spectral information that can be collected when imaging in scattering tissue, such as in animal models, by using the optical output device 50, which divides the detected light spectrum into multiple broad color channels, and the tunable optical channel filters 60, which divides successive, multi-channel image frames into a number of distinct wavelengths.

Figure 5:
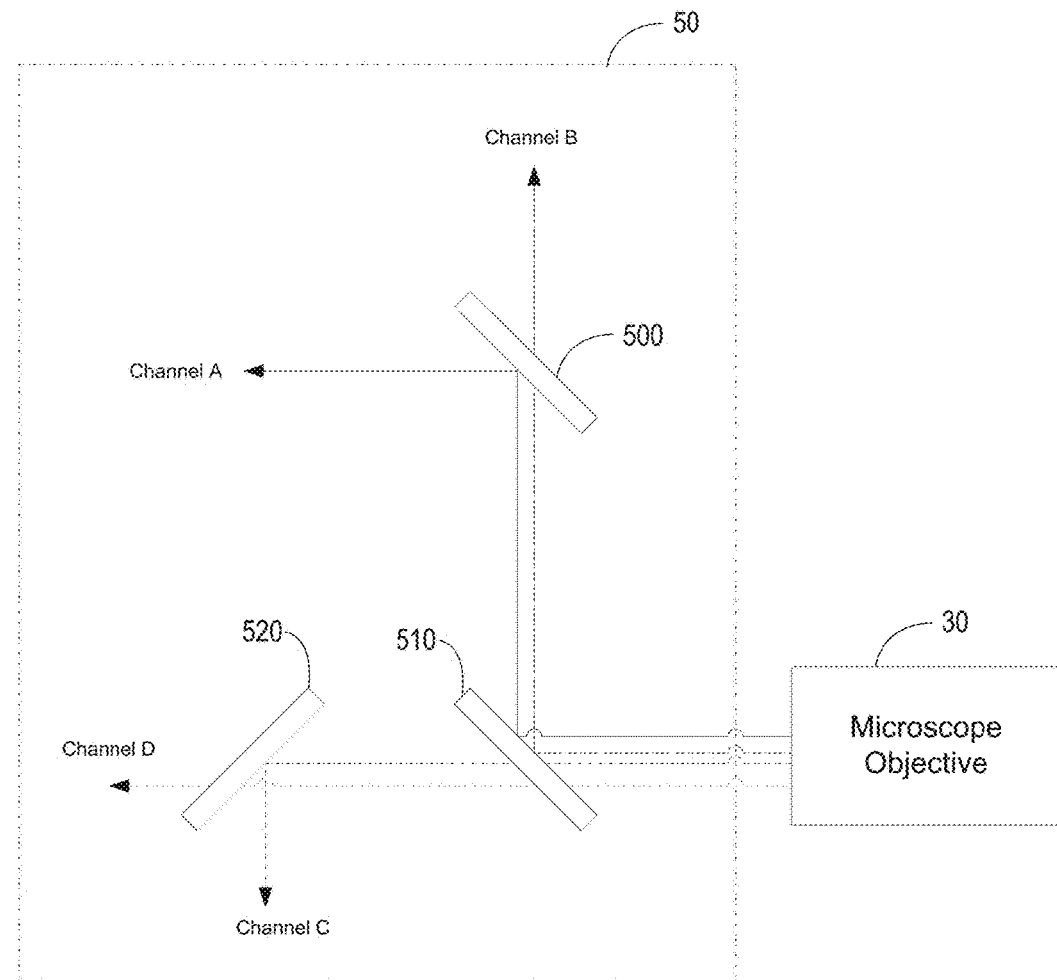
FIG. 5 illustrates an example configuration of an optical output device.

The optical output device 50 may include one or more wavelength-selective optical devices. As illustrated in FIG. 5, the wavelength-selective optical devices may be dichroic mirrors 500, 510, and 520. The dichroic mirrors 500, 510, and 520 are placed before each "channel" to divide the detected light spectrum into broad color channels. The dichroic mirrors 500, 510, and 520 may be fixed wavelength dichroic mirrors. In an implementation, the detected light spectrum may be divided into four channels each spanning about 75 nm. Although not illustrated, the hyperspectral multiphoton microscope disclosed in this document may further include lenses that are placed before the optical output device 50 and are used to send light through the optical output device 50.

Figure 6:
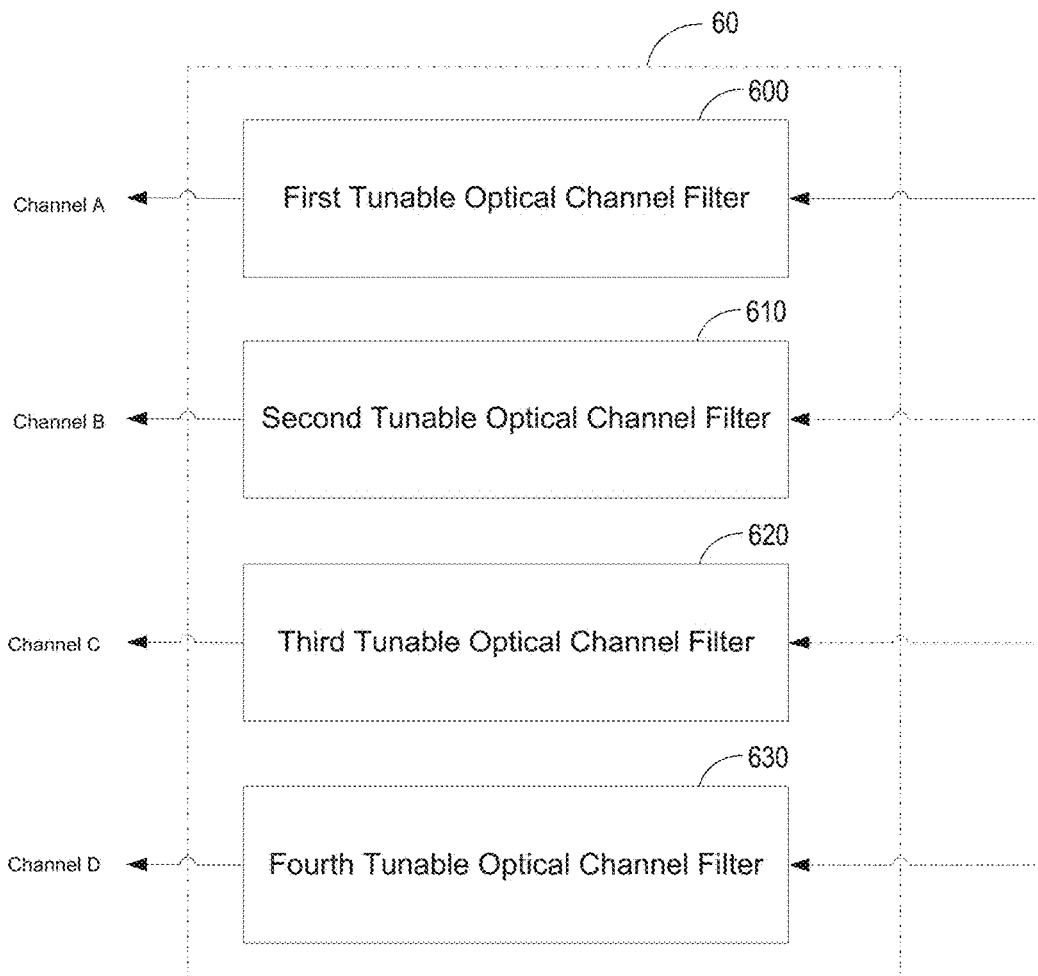
FIG. 6 illustrates an example configuration of tunable optical channel filters.

FIG. 6 illustrates an example configuration of the tunable optical channel filters 60. A detection system of the hyperspectral multiphoton microscope disclosed in this document includes one or more "channels." In an implementation, for the tunable optical channel filters, angle-tunable bandpass filters with 20-nm spectral passband may be used at multiple different angles in successive image frames. In an implementation where the detected light spectrum is divided into four channels and the angle-tunable bandpass filter is used at four different angles, the end result converts these successive, multi-channel image frames into a single image that has a number of distinct imaged wavelengths equal to the number of fixed channels multiplied by the number of angles used. Thus, four successive four channel images each taken at a different angle of the bandpass filters produces a single 16 channel image with about 20-nm spectral resolution across the full visible spectrum. If this process is repeated for three different excitation lasers, therefore, 48 images, representing different excitation and emission combinations, can be obtained. By further dividing the wavelength span of each broad color channel into a number of distinct fluorescent imaging wavelengths, images of multiple fluorescent markers can be obtained. In another implementation where the light source 10 utilizes a rapidly-tunable laser, tuned to several consecutive wavelengths, more optical wavelength images can be obtained consecutively.

Figure 7:
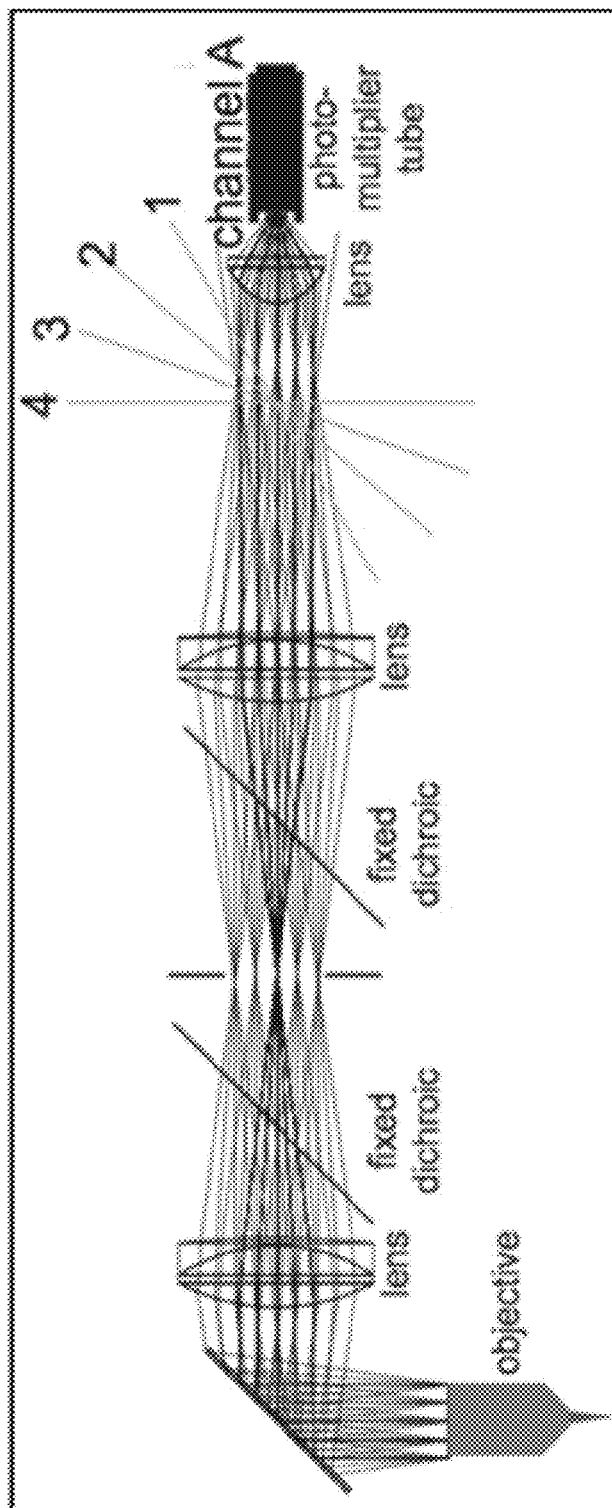
FIG. 7 illustrates an example of a detection system of the hyperspectral multiphoton microscope each channel of which detects a band of fluorescent emission light.

FIG. 7 illustrates an example of the detection system of the hyperspectral multiphoton microscope each channel of which detects a band of fluorescent emission light (e.g., the light emitted by the sample) as determined by fixed dichroic mirrors placed to divide the emitted light spectrum. A telescope for each channel, having multiple lenses, sends light through an angle-tunable bandpass filter 600, and condensing lenses, which are placed after the angle-tunable bandpass filter 600, focuses light onto a photomultiplier tube. In an implementation, each channel has the angle-tunable bandpass filter 600 used at four different angles, and can obtain four distinct wavelength images (i.e., one wavelength image for each angle). Large area optics collect a divergent cone of light exiting from the back aperture of the microscope objective, retaining the signal from scattered photons from deep in the sample. This allows imaging at greater depths in scattering tissues.

Figure 8:
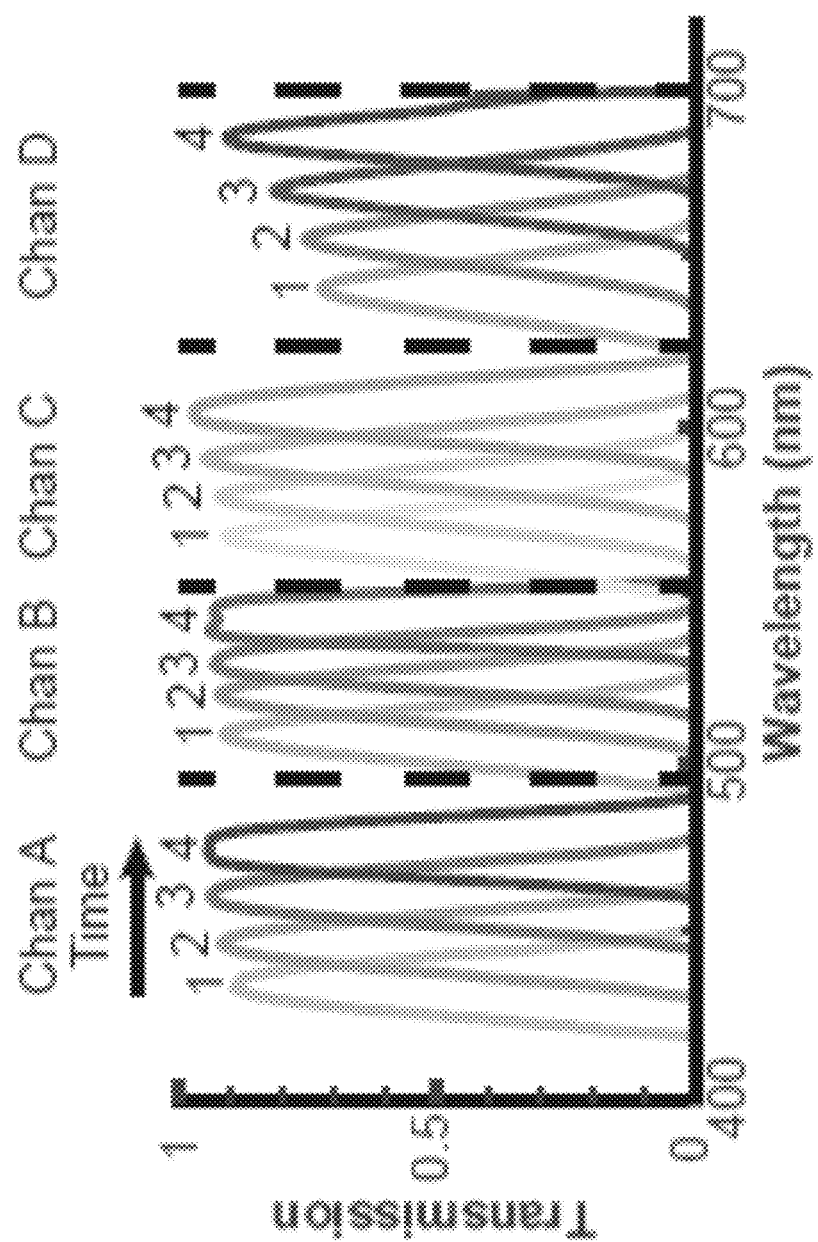
FIG. 8 illustrates lambda stacks generated by collecting images for a combination of excitation laser wavelengths and filter angles.

FIG. 8 illustrates lambda stacks generated by collecting images for a combination of excitation laser wavelengths of the light source 10 and filter angles of the tunable optical channel filters 60. In an implementation where the detected light spectrum is divided into four channels and the angle-tunable bandpass filter is used at four different angles, four successive four channel images each taken at a different angle of the bandpass filters produces a single 16 channel image with about 20-nm spectral resolution across the full visible spectrum. This whole process can then be repeated with different wavelength excitation lasers. As discussed above, if three different excitation lasers are used, 48 optical wavelength images of multiple fluorescent markers can be obtained simultaneously.

Figure 9:
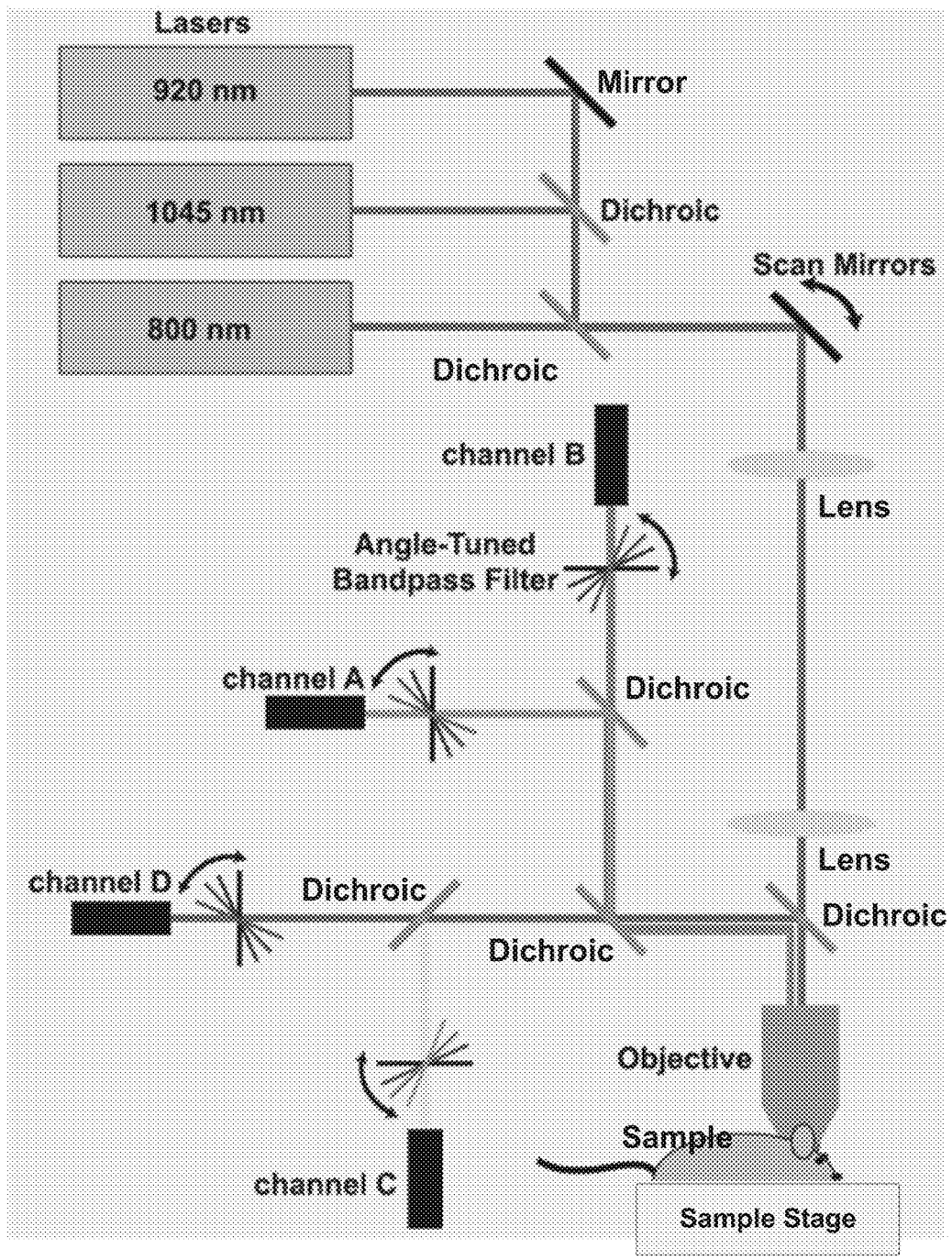
FIG. 9 illustrates an implementation that uses three different excitation lasers.

FIG. 9 illustrates an implementation that uses three different excitation lasers. In this implementation, the light source 10 may generate three excitation laser beams having wavelengths of 800 nm, 920 nm, and 1045 nm, respectively. In an implementation where three different excitation lasers are used, the detected light spectrum is divided into four channels, and the angle-tunable bandpass filter is used at four different angles, a 48-channel image can be made. To collect three-dimensional data, the sample positioner 42 is then moved relative to the laser focus and the process starts from the beginning. The disclosed technology can be implemented in various ways to provide similar or complimentary datasets. The detectors can be implemented in various configurations and may use various kinds of photomultiplier tubes (e.g. bialkalai, or GaAs), or may use avalanche photodiodes. In another implementation, the angle-tunable bandpass filters may be replaced by acousto-optic tunable filters or filter wheels that rotate between several fixed wavelength filters. The excitation laser(s) may be a number of individual lasers tuned to separate wavelengths, or a rapidly-tunable laser, tuned to several consecutive wavelengths. The detection system can contain a variable number of detection channels by dividing the detected light spectrum into multiple channels at the optical output device 50 (ideally 2-4, although more are possible).

Figure 10:
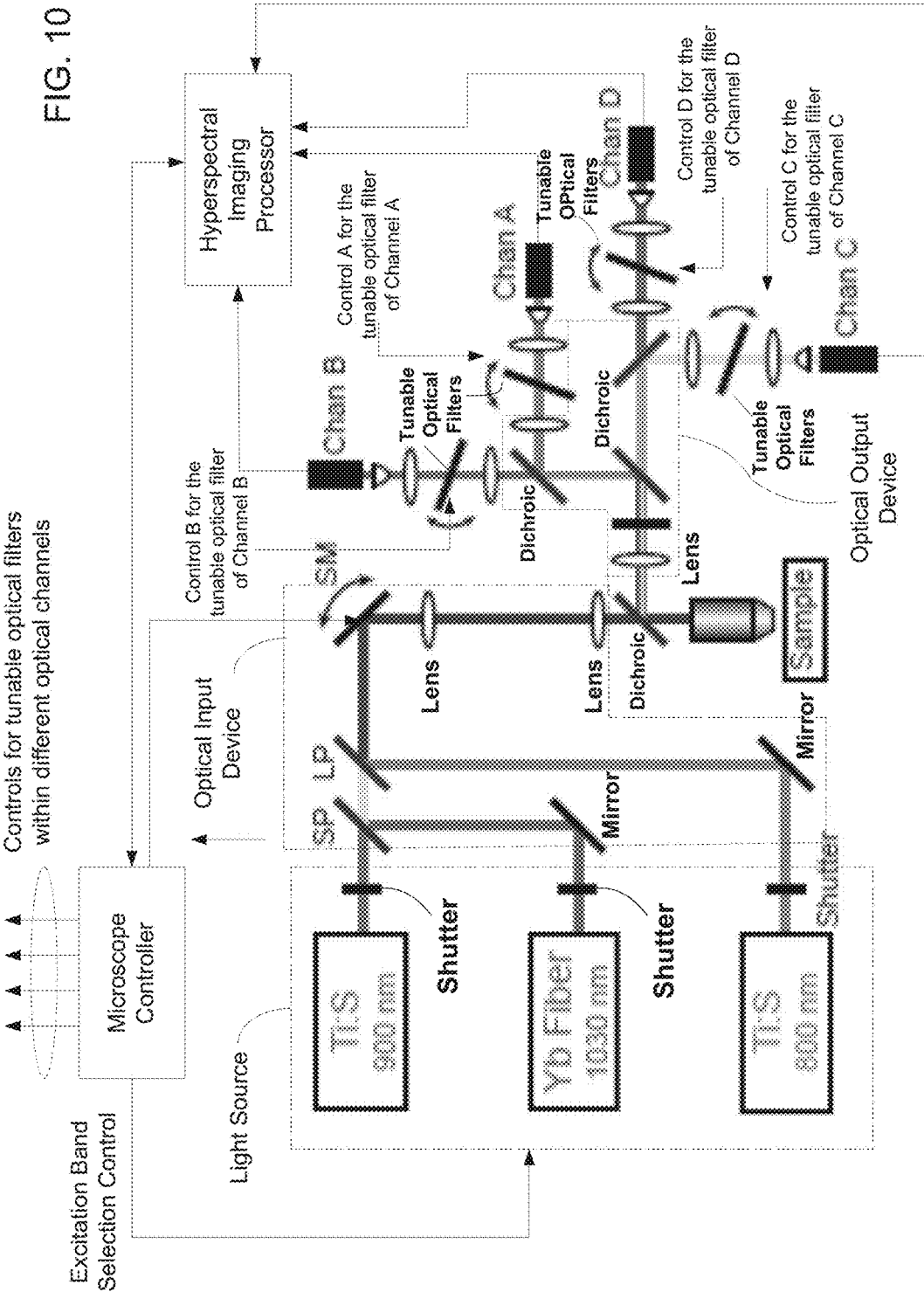
FIG. 10 illustrates another implementation that uses three different excitation lasers.

FIG. 10 illustrates another implementation that uses three different excitation lasers. In this implementation, a light source generates three excitation laser beams having wavelengths of 800 nm, 900 nm, and 1030 nm, respectively. The excitation laser beams are directed to a sample by an optical excitation input device. The optical excitation input device combines the three excitation laser beams into one laser beam using two mirrors and a combination of short pass and long pass dichroic mirrors SP and LP. A scan mirror SM placed between the combination of short pass and long pass dichroic mirrors SP and LP and the sample allows the laser beam to be redirected to a microscope objective to scan the sample. A plurality of lenses arranged along the light path of the laser beam can condense the light onto the sample and image the scan mirrors to the back aperture of the microscope objective to facilitate scanning of the sample. An optical emission output device has a plurality of dichroic mirrors to divide light emitted from the sample and sent to the optical emission output device through the microscope objective. The optical emission output device collects a divergent cone of light exiting from the back aperture of the microscope objective, retaining the signal from scattered photons from deep in the sample. Tunable optical filters (e.g., angle-tunable filters) are placed in front of each photomultiplier tube to improve the spectral discrimination. In addition, three different-wavelength, femtosecond laser sources are routed into the system to provide a range of excitation conditions.

Detection optics are ray-traced to collect as much of the divergent cone of light coming from the back aperture of the objective as possible. In some implementations, hyperspectral images are acquired by alternating laser excitation source and the positions of the tunable optical filters on a frame-by-frame basis. To compensate for differences in the photomultiplier tube gain, a calibration technique may be used by imaging a calibration light source and calculated appropriate image scaling factors for the photomultiplier tube gain settings. A hyperspectral imaging processor gathers spectral information collected when imaging in scattering tissue and uses it to obtain spectral images. A microscope controller may control the operations of the light source, the optical excitation input device, the tunable optical filters, the motion of the scan mirrors, the motion of the sample stage, and the hyperspectral imaging processor. For example, the microscope controller provides control signals for tunable optical filters within different optical channels. Specifically, the microscope controller may control the operation of the light source so that different excitation laser beams at the different selected excitation laser wavelengths can be sequentially selected and directed to the sample. The microscope controller may also adjust filter angles of the tunable optical filters. The microscope controller may communicate with the hyperspectral imaging processor to control the acquisition and processing of hyperspectral images.

In the examples shown in FIGS. 9 and 10, due to the optical design for collecting the fluorescent light from the sample by the microscope objective to each optical detector in each optical channel, all available fluorescent light at each fluorescent imaging wavelength within a corresponding designated fluorescent imaging wavelength band in the corresponding optical channel output beam is collected and directed to the corresponding optical detector subject to the effective optical numerical aperture along the optical path without using an optically dispersive element in the optical path. Specifically, all the fluorescent light collected by the microscope objective can be collected via the dichroic reflectors and the angle tunable optical passband filter in each channel to reach the optical detector in the channel. In comparison, some other systems based on optically dispersive elements, such a dispersive element spatially separates collected fluorescent light from a sample into different light beams at different fluorescent imaging wavelengths and the optical aperture for collection of such spatially separated beams at different wavelengths is inherently limited. Given the relatively weak signal in fluorescent emission caused by nonlinear absorption, optical detection based on optically dispersive element can comprises the signal collection efficiency and the overall signal to noise ratio.

Figure 11:
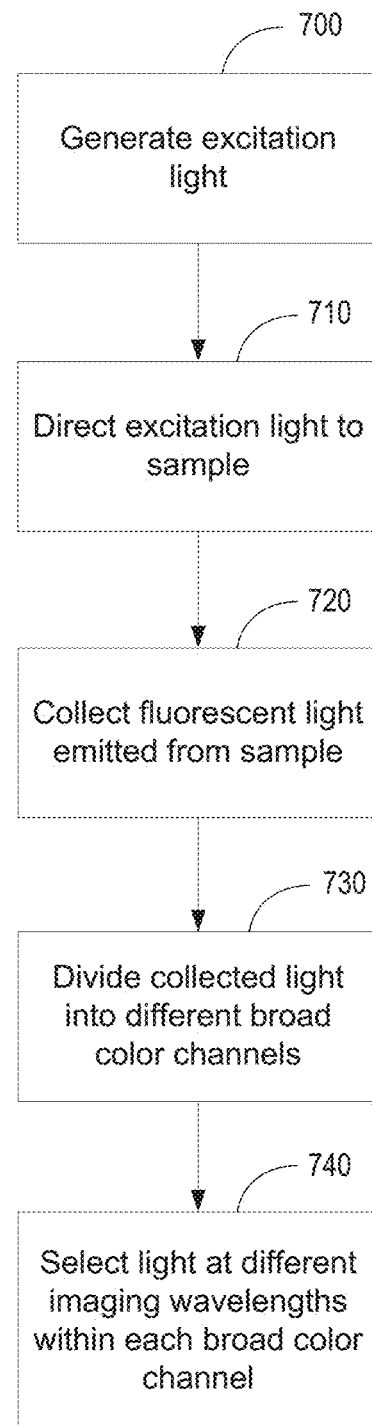
FIG. 11 illustrates a method of acquiring fluorescent emission spectra from a sample.

FIG. 11 illustrates a method of acquiring fluorescent emission spectra from a sample based on the two-stage spectral separation to obtain hyperspectral imaging. This particular example includes collecting images simultaneously from each detector for a series of detection bands (e.g. filter angle) for each laser wavelength. The method of acquiring fluorescent emission spectra includes a plurality of steps 700, 710, 720, 730, and 740. At the step 700, multiple lasers tuned to separate wavelengths are generated and sent to the microscope objective 30 through the optical path 20. After the multiple lasers have passed the optical path 20, they are directed toward the sample 40 at the step 710. Each of the multiple lasers independently excites fluorophores with distinct multiphoton absorption spectra in the sample 40 and causes the sample 40 to emit light. At the step 720, the light emitted by the sample 40 is collected and sent to the channel divider 50. The method of acquiring fluorescent emission spectra from a sample in this implementation includes two separate steps of distinguishing the multiphoton absorption spectra from others. Once the light emitted by the sample 40 is collected, a first spectral separation is performed at the step 730 by selecting a particular wavelength span for each channel, for example, at dichroic mirrors. Subsequently, at the step 740, a second spectral separation is performed by using angle-tunable bandpass filters in order to further separate out different wavelength bands. The second spectral separation is performed by angle tuning of angle tunable bandpass filters. Here, in detecting the separated wavelengths, various detection electronics such as photon integration and photon counting may be used.

Specifically, a method of imaging a sample based on nonlinear optical absorption and emission in the sample begins with directing to a sample different excitation beams at different excitation wavelengths that interact with the sample to cause nonlinear optical absorption of two or more photos at each excitation wavelength to emit light at one or more fluorescent emission wavelengths different from the corresponding excitation wavelength. By operating a microscope objective, the excitation beams are directed toward the sample stage to illuminate the sample and to collect light from the sample. The collected light at the microscope includes returned excitation light at the excitation wavelengths and emitted light via nonlinear optical absorption at fluorescent emission wavelengths. Then, from the collected light by the microscope objective from the sample, the emitted light at the fluorescent emission wavelengths by the sample is selected as an output beam while excluding light at the excitation wavelengths from the output beam. Subsequently, the output beam is separated into different optical channel output beams along different optical channel optical paths at different designated fluorescent imaging wavelength bands, respectively. By operating different optical channel filters in the different optical channel optical paths, respectively, the different optical channel output beams at the different designated fluorescent imaging wavelength bands are received and filtered. Each optical channel filter spectrally selects light within a corresponding designated fluorescent imaging wavelength band to be in a corresponding optical channel output beam. By operating different optical channel detectors located along the different optical channel optical paths, each optical channel detector receives a corresponding optical channel output beam and produces an optical channel detector output having information of the sample at within a corresponding fluorescent imaging wavelength band for the corresponding optical channel output beam.

In another implementation, excitation lasers are rapidly switched between each frame for a given detection band, and the plurality of steps 700, 710, 720, 730, and 740 discussed above may be repeated for each detection band. By alternating laser excitation source and the positions of angle-tunable bandpass filters on a frame-by-frame basis, hyperspectral images may be acquired. In addition, a calibration technique may be used to compensate for differences in the photomultiplier tube gain by imaging a calibration light source and calculated appropriate image scaling factors for the photomultiplier tube gain settings.

The hyperspectral multiphoton microscope disclosed in this document will uniquely enable high optical-resolution, simultaneous imaging of many fluorescent labels, even with significant spectral overlap, deep into scattering tissue. Existing instruments either provide deep imaging but lack sufficient spectral resolution to cleanly separate fluorescence signatures (e.g. standard two-photon excited fluorescence microscopes with 1-4 fluorescence detection channels), or they provide dense spectral data but cannot image deep into scattering tissue (e.g. commercial hyperspectral confocal and multiphoton microscopes that rely on prisms or gratings for color separation). Such limitations have hampered the otherwise clever use of combinatorial fluorescent protein expression to generate unique spectral signatures for distinguishing individual cells. The "Brainbow" mice use the stochastic activation of a number of different colors of fluorescent proteins (XFPs) via a tamoxifen-inducible promoter to label neurons with hundreds of unique spectral signatures that can be used to distinguish individual cells. Because these colors are passed on to a cell's progeny after division, this also provides a way to lineage trace the descendants of stem cells. Using such labeling approaches, the hyperspectral multiphoton microscope disclosed in this document will open up a whole new class of in vivo imaging experiments, where most to all cells in a tissue volume are labeled and their dynamic behavior and interactions can be directly observed and followed. Rather than limiting in vivo imaging to the hypothesis testing mode described above, this capability to image the dynamic interactions of all cells in the imaged volume over time could be used to generate novel hypotheses about the cellular interactions that drive normal and disease state physiological processes, a new role for live animal imaging in biological and biomedical research. The additional spectral resolution gained will also facilitate identification of unknown autofluorescent species in tissue, as well as provide high-sensitivity in measurements that depend on spectral signatures, such as fluorescence resonance energy transfer (FRET). For experiments involving multiple cell types, such as in immunology studies, this instrument will allow labeling each cell type with a unique fluorescent label, regardless of label similarity (e.g. green fluorescent protein [GFP] and FITC, which have very similar emission spectra). Lessening constraints due spectral overlap will give researchers the flexibility needed to use well-tested fluorescent labels.

Figure 12:
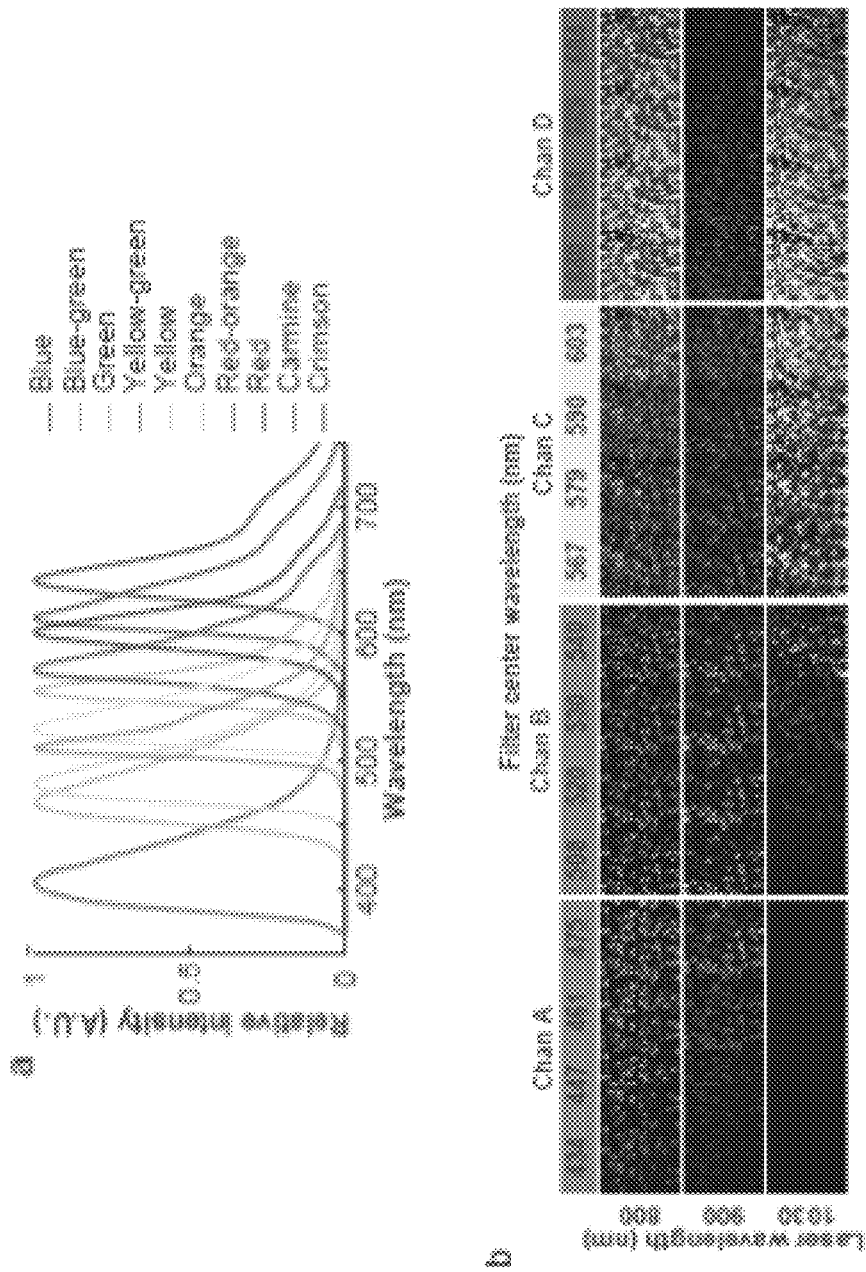
FIG. 12 shows the ability of the hyperspectral multiphoton microscope to differentiate highly-overlapped fluorescent labels.
Figure 12:
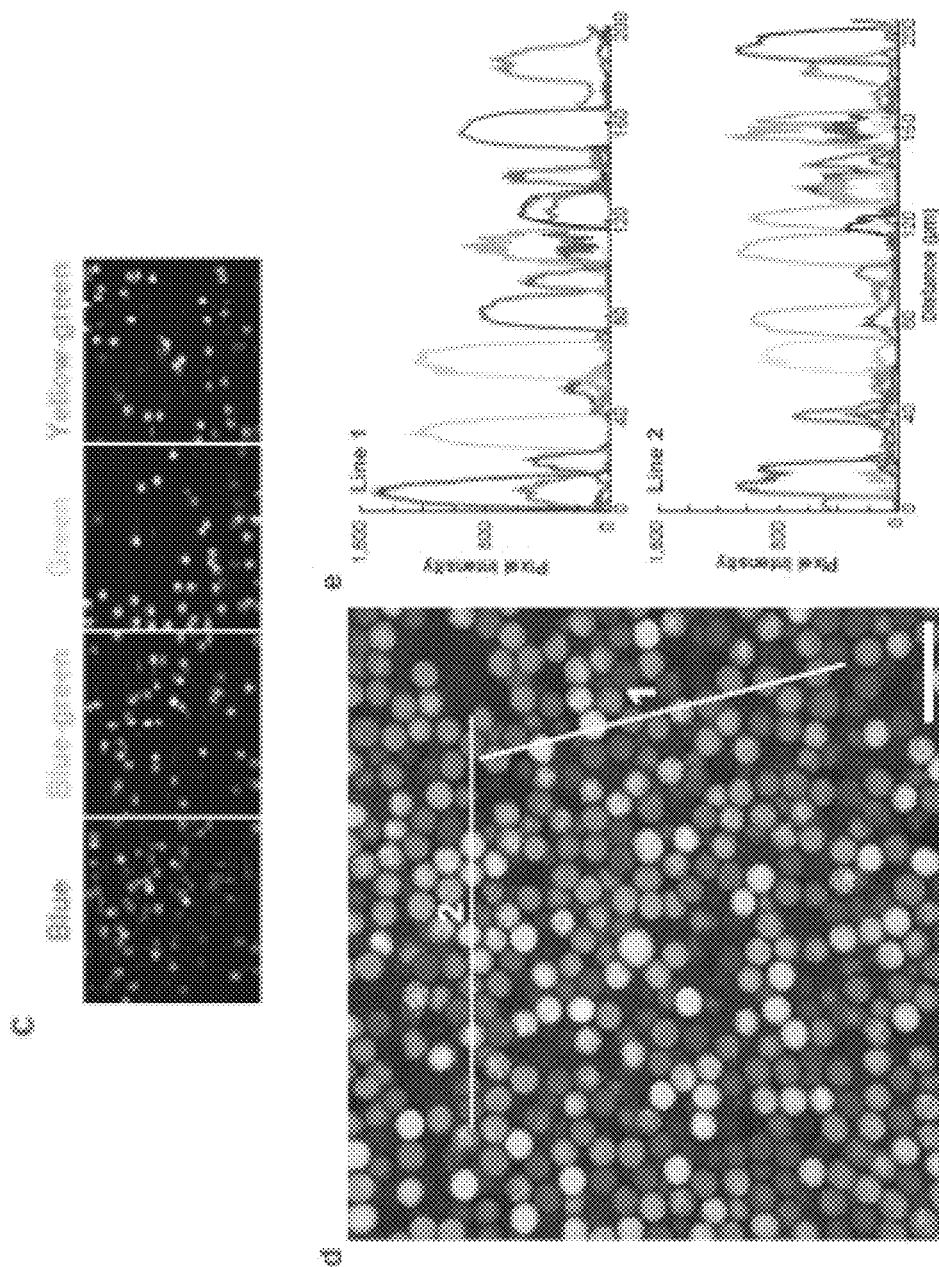
Figure 12:
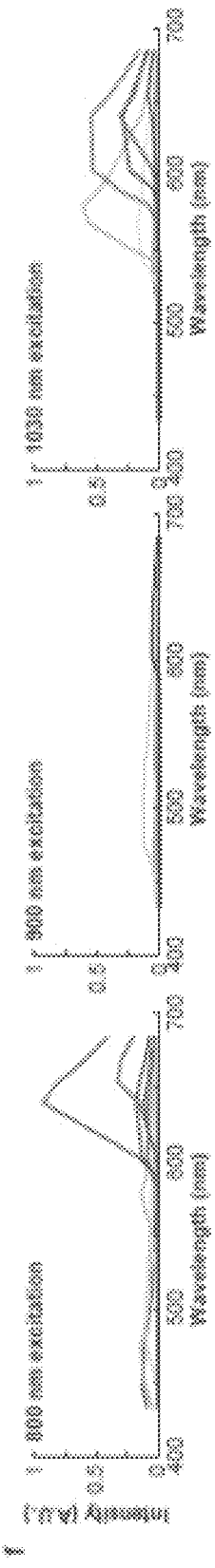

Referring to FIG. 12, the ability of this microscope to differentiate highly-overlapped fluorescent labels can be demonstrated by imaging ten colors of fluorescent polystyrene beads embedded in agarose gel. FIG. 12(a) shows fluorescence emission spectra of the ten bead colors. In FIG. 12(b), a 48-channel image array of the bead sample acquired at a given laser wavelength is shown in rows, and at a given filter angle in columns (denoted by the passband center wavelength). The colored bands indicate the four broad color channels Chan A-D. FIG. 12(c) illustrates unmixed images of individual bead colors. A 48-channel hyperspectral image was acquired for the bead mixture of FIG. 12(b), and for samples containing only one bead color (data not shown).

Spectral end-members are extracted from the single-color samples and used to unmix the image of the mixed-bead sample. Then beads are selected in the mixed bead image that represents the ten different colors (now easily distinguishable after the first iteration of unmixing). Subsequently, a refined set of spectral end-members is created to be used to, again, unmix the 48-channel image of the mixed bead sample, yielding an image with ten separate color channels. FIG. 12(d) illustrates a false-color composite image of spectrally unmixed bead sample. Some beads appear to range in size from 15 µm to 20 µm in diameter. FIG. 12(e)

illustrates intensity values of beads for all 10 channels across Lines 1 and 2 in FIG. 12(*d*). FIG. 12(*f*) illustrates calibrated bead spectra across the three excitation lasers measured using the hyperspectral multiphoton microscope.

The example of the hyperspectral multiphoton microscope disclosed in this document utilizes angle-tunable bandpass filters with high transmission efficiencies placed before individual photomultiplier tubes, which have high quantum efficiencies relative to photomultiplier tube arrays. The hyperspectral multiphoton microscope provides in vitro and in vivo imaging of multiple fluorescent markers, with solid calibrations. By using the hyperspectral multiphoton microscope, the demonstrated spatial resolution can be extracted from the microscope images, and the resolution is just under 0.5 µm laterally, about 1 µm axially. A hyper spectral imaging using the hyperspectral multiphoton microscope can be done at depths of about 200 µm. The hyperspectral multiphoton microscope disclosed in this documents is capable of separating highly overlapped fluorescent species, for example, 10 different overlapped fluorescent beads, 7 different fluorescent markers in live cells, and 5 or 6 in live mouse brain.

In designing a microscope based on nonlinear optical absorption in fluorescently-labeled structures within the sample for hyperspectral imaging, various factors may be considered. For example, optical scattering from tissue may significantly impact the device's ability to image deep in a sample, and the types of samples to be imaged.

In general, the structure of the tissue of interest—cells, subcellular organelles, and extracellular matrix elements such as collagen—provides a challenge for imaging in vivo. Scattering can be caused by misdirection of light due to points of a spatially varying refraction index profile at different locations of the sample. These tissue strictures act as scattering elements for both the excitation laser and fluorescence. For shallow depths or nearly transparent samples, photons emitted at the focal volume travel in a ballistic trajectory toward the microscope objective. Few scattering elements exist to impede photon travel. This trajectory is within the numerical aperture (NA) of the microscope objective and leads to high light collection efficiencies. However, in scattering samples, especially at depth, photons experience multiple scattering events during the return to the tissue surface and no longer enter the objective via a ballistic trajectory. Photons outside the acceptance angle of the objective are no longer collected, leading to lower detection efficiencies. When fluorescence is generated deep in tissue, the fraction of light that is generated for a fixed laser power exponentially decreases with depth, in addition to scattering loss of emission photons. The laser power can be increased to generate more fluorescence for detection, but at a certain point, the photon flux is so high at the surface of the tissue that fluorescence is generated out-of-focus, leading to a high background signal (termed the surface to background-ratio, or SBR). This can limit the imaging depth for 2PEF microscopy.

Scattering can be highly wavelength dependent, and an important factor in choosing the laser wavelength for excitation. Scattering decreases with longer wavelength, so generally the use of long wavelength light guarantees deeper imaging capabilities, in addition to lower phototoxicity. This factor makes the longer wavelengths of light necessary for 2PEF more attractive in some applications. In addition, scattering affects the transmission of generated fluorescence, with blue wavelengths scattering more than red wavelengths. Therefore, fluorophore selection for deep imaging favors red and far-red fluorescent labels.

While it is nearly impossible to predict the exact scattering characteristics of a tissue for imaging, many models exist based on scattering theory and measurements made in a variety of tissue types. Typically, scientists use the Mie model for scattering to predict tissue light diffusion, where the tissue is represented as a medium with scattering spheres of a higher refractive index. The amount of scattering varies as $(1/\lambda^{0.5})$, with longer wavelengths producing less scatter. When the scattering elements are much smaller than the wavelength of light, which is a limit of the Mie regime, the Rayleigh regime, predicts a much greater dependence on wavelength $(1/\lambda^4)$. Other models incorporate continuous variations in refractive index that may better capture the multicomponent structures of cells (cytosol, and scattering elements like the nucleus, mitochondria, etc.). Regardless of the model, particularly dense or opaque tissues, such as bone, muscle, cartilage are more difficult to image due to high scattering, although it is possible at shallow depths. Tissues such as cerebral cortex and dermis are more transparent, and enable deeper imaging, especially at long wavelengths.

For standard, 2PEF experiments in vivo, detection is entirely epifluorescent. That is, a detector is not, and cannot, be placed opposite the laser source to collect forward-scattered fluorescence. Therefore, the detected fraction consists of 1) ballistic photons, and 2) scattered photons with original trajectories away from the objective, but scatter in a trajectory that enables objective detection. 2PEF is an isotropic process, with photons emitted equally in all directions around the focal volume. Therefore, a photon generated by a fluorophore in a scattering sample may experience different scattering situations, e.g., 1) ballistic emission and detection, experiencing no scattering events, 2) continual scattering in tissue until it is absorbed, 3) exit from the tissue surface, but either missing the objective entirely or incident on the objective front aperture at an angle beyond the objective NA, or 4) exit from the tissue, despite scattering, and collection by the objective. Beaurepaire et al. showed that, up to moderate depths, scattering actually increases the detected signal fraction, as both ballistic and a subset of scattered photons are detected. For greater depths, scattering leads to a decrease in collection efficiency scaled as $z^{-2}$. The NA plays a key role in detection, with the collected power scaling proportional to $\theta^2_{NA}$ for different depths. At the surface of the sample, highly scattered fluorescent signal forms a diffuse radius, so a large FOV also increases fluorescence detection efficiency. Therefore, a high NA, low zoom objective can be used to improve optical detection for scattering samples.

An important repercussion of collecting a wide distribution of photon angles in scattering samples is the divergent cone of light exiting the objective back aperture (OBA). For 2PEF, where every photon contributes to the signal to improve the signal-to-noise ratio (SNR), it is beneficial to collect as much light as possible from the entire cone of light. Some commercial systems, with standard one inch diameter optics, severely clip the outer rays of this cone, leading to loss of signal at depth (by a factor of ~3 when compared with a system designed with larger aperture optics). Some custom multiphoton microscopes now favor the use of large aperture lenses for collection, in addition to minimal sample-to-detector distances.

In designing a microscope based on nonlinear optical absorption in fluorescently-labeled structures within the sample for hyperspectral imaging, fluorescent label choices should be carefully designed for imaging biologically complex samples.

Choosing proper fluorescent labels can be important part of the multiphoton imaging with respect to certain aspects of fluorescent labeling, such as specificity, brightness, stability, and color palette. Specificity refers to how specifically a fluorophore labels a structure of interest versus other structures. A fluorophore that labels all components of all cells may be ineffective, as there would be no contrast between a structure and its surrounding. For some studies, labeling an entire cell population may be suitable or desirable. For example, CX3CR1 GFP mice have been engineered to express green fluorescent protein (GFP) in the same cells that express the chemokine receptor CX3CR1, such as in microglia in the brain. However, the researcher must be aware that other cells, such as macrophages, also express CX3CR1 and thus will be GFP-positive. To tell macrophages apart from microglia, another method may be used for labeling. One such method, for example, is to acquire macrophages from another mouse, expressing a different color protein, and transfer them to an irradiated CX3CR1 mouse via bone marrow transplantation. Microglia, which remain resident in the brain, will express GFP, and macrophages, produced by the transplanted bone marrow, will express the other fluorescent label. Combination techniques like this are common when ensuring specificity of labeling in studies, and require a thorough understanding of the biology involved.

Different methods can be used to enable specificity. Generally, labels or labeling substances may be categorized as exogenous (dyes and fluorescently tagged antibodies), endogenous (auto fluorescence or SHG/THG), or transgenic organisms. Many exogenous fluorescent dyes tend to localize to specific structures upon application, providing automatic specificity. For example, Hoechst preferentially labels DNA and localizes in the nucleus. Injection of a dye into vasculature is commonly used for blood vessel visualization. Another exogenous labeling method, antibodies conjugated to a fluorescent protein, can also be designed to target specific antigens on structures of interest, providing targeted labeling. However, antibody labeling is difficult in vivo, especially in the brain where the blood brain barrier prevents materials from exiting vasculature into the surrounding tissue. Endogenous fluorescent species, such as NADH or riboflavin, often fluoresce at shorter excitation wavelengths, and can provide insight into both structural and metabolic information in the tissue. Transgenic methods tie a gene for a fluorescent protein to a promoter, enabling the cell itself to produce the fluorescent protein. This is especially useful in vivo, where a fluorescent protein gene is tied to a promoter specific to a cell population or subcellular compartment. For example, in the CX3CR1-GFP mice mentioned previously, CX3CR1 is the promoter and GFP is the fluorescent protein. Stable transgenic animal lines with fluorescent expression can be important to most in vivo two-photon experiments.

Fluorescent label brightness and stability should be carefully considered, as dim fluorophores lead to low SNR images and unstable labels lose their fluorescence quickly. The brightness of a fluorophore is a function of its absorption cross section (a measure of its efficiency as a function of wavelength). Although the emission is identical for a fluorophore despite one- or two-photon excitation, the absorption profiles can vary greatly depending on the molecule symmetry. Typically, two-photon cross sections are much broader, and may contain additional peaks. Bright labels with a high two-photon cross-section may be chosen to excite the label at its peak absorption, when the cross-section information is available. Stability also depends on the fluorophore's chemical structure. Certain labels become easily damaged when excited by a laser source, termed photobleaching. The chemical structure of the label itself is altered and it is no longer able to fluoresce. Almost all labels will photobleach at high enough laser powers, so care must be taken while imaging to maximize SNR in an image by controlling PMT gain and laser power, while minimizing photobleaching In addition, the color palette of labels used in a single experiment may be restricted. Although fluorophores exist in almost any color, the fluorophore emission profile is very wide (~80-200 nm). Use of more than two or three labels leads to inevitable spectral overlap, as the visible spectrum is limited to 400-700 nm. Spectral overlap between detection channels, or bleed-through, leads to images where structures appear in multiple channels. When all structures have visually obvious morphological differences, spectral bleed-through is more of an annoyance than a critical experimental flaw. However, when visually identical cells are only specified by their fluorescent label color, or cells are closely packed and overlapping, this could lead to misidentification of cell types.

The spectral overlap can be minimized by choosing colors as far apart as possible. This is typically blue and red, or green and red for a two-color experiment, and blue, green, and red for a three-color experiment. Colors are separated by choosing dichroic mirrors to split fluorophore emission between fluorophores, and filters are chosen to collect light primarily from the emission peak of each label. However, in experiments with multiple cell types and fluorophores, multiplexed approaches can be used to differentiate overlapping labels for clear identification of multiple cell types.

In designing a microscope based on the above disclosed technology, the laser source can be designed to provide short, high peak power pulses for optimal 2PEF signal generation. In addition, fluorophore excitation requires the ability to change the laser wavelength for the brightest fluorescent signal. Having the ability to tune wavelength allows broad two-photon excitation spectra and excite several fluorophores with the same laser source. In some designs, Titanium:Sapphire (Ti:Sapph) lasers can be used based on their short pulse duration (50-300 fs), tunability (~680-1020 nm), and relative ease of use. A number of manufacturers, particularly Coherent, produce turn-key systems favored by researchers for this purpose. Ytterbium-doped fiber (Yb:fiber) sources (Amplitude Systèmes and IMRA) provide a fixed wavelength solution (~1040 nm) preferable for excitation of red proteins. Two important laser parameters for consideration are the laser repetition rate and pulse energy. A dim dye, with a low two-photon cross section (a measure of how bright it fluoresces when two-photon excited, in units of Goeppert-Mayer, or GM) requires high energy, while bright dyes perform well at low energy and a wider range of repetition rates. Having a high pulse energy eventually leads to ablative damage, a nonlinear process that causes instantaneous ionization of material in the laser focus. A combination of high laser repetition rate and power leads to thermal damage, which must be avoided for biological studies. Therefore, a laser with a repetition rate between 1 MHz and ~100 MHz is suitable for simultaneous excitation of both dim and bright dyes, with care not to saturate bright dyes.

In addition, the optics used to route the laser source should be properly designed. A pulse short in time contains many wavelength components, typically a Gaussian profile with a bandwidth of ~50 nm. Due to dispersion of a glass, bluer wavelengths travel in the glass slower than red wavelengths, leading to pulse stretching. To compensate for dispersion, compressor optics may be placed outside of the laser, between the laser and the sample. The dispersion compensation can be tuned based on the specific microscope configuration Before the laser is routed to the microscope, either an electro-optic modulator (EOM) or a combination of waveplates and polarizing beamsplitter cubes is used to provide continuous tuning of laser power delivered to the microscope. The laser power can be selected to maximize signal without saturation or thermal tissue damage, and vary power based on imaging depth.

Due to the nonlinear nature, 2PEF only occurs within the focal volume which is scanned throughout the sample to generate an actual image. In some designs, galvanometric scan mirrors may be used for this canning with two orthogonal small mirrors each attached to a small rotating motor, providing custom control of scan patterns by controlling each independent motor. When routed through a telescope for beam expansion (termed the scan and tube lens), the angular direction of the laser beam is mapped to the back aperture of the microscope objective. This translates to various positions in x and y in the FOV of the microscope objective. In order to achieve the best resolution from the microscope objective, the beam can overfill, or be larger than, the back aperture of the objective. The larger the scan mirrors, the easier it is to magnify the beam to the correct size, but the slower the image acquisition speed since the mirrors themselves provide more inertia. To capture cellular dynamics in vivo, an image line speed of approximately 1 kHz is recommended. Another option is to use resonant scan mirrors, which oscillate at a fast, but fixed speed.

The choice of microscope objective depends greatly on the experiment itself. For optimal resolution, a high NA (implying a small focal volume) is preferred. Since the same objective is used for detection, the wide cone of acceptance angles from the sample increases the ability to collect signal diffusing from the sample. However, this high NA implies a tradeoff in terms of a small working distance that is difficult with many biological samples, and a small FOV. Very high NA objectives also often require oil immersion, which is often incompatible with live animal preparations. Another option is to use a low NA objective, which provides a wide FOV, but low resolution and detection efficiency. Most multiphoton users that experiment with live animal preparations often use a low NA (low magnification) objective to create a large FOV "map", and then a moderately high NA objective with a long working distance and water immersion to perform detailed imaging.

The optical transmittance of the microscope objective is a key parameter to consider for both visible and near-infrared wavelengths. An objective with high transmission across this range (~350-1100 nm) limits laser attenuation through the objective and loss of signal light from the sample.

In some designs, scan mirrors can be used to provide x-y translation, but the sample itself (or the microscope objective, in certain setups) can be translated in the z-axis. Most multiphoton setups have a three-axis motorized stage for the sample, enabling rapid adjustments of overall sample position beneath the objective and small, finely-tuned, micrometer-level adjustments during imaging. For experiments involving elaborate sample paraphernalia (patch clamp, incubator, live animal maze/wheel, etc.), a large area beneath the microscope itself is required.

For the detection optics for multiphoton microscopes, since fluorescence is only generated at one point in the sample, so the detection system should be designed to collect as much light as possible from the focal volume and map it to the proper color detector. The position of the focal volume is controlled by a signal to the scan mirrors, so software attributes the signal to the right pixel. A long-pass dichroic mirror placed directly above the microscope objective diverts visible-wavelength fluorescence from the sample toward the detection optics, while allowing laser excitation light to pass through. To block any laser light that may scatter into the detection optics pathway and saturate the detectors, a short-pass blocking filter is typically placed at the entrance of the detection optics, or in front of each detector. The detectors may be implemented by photomultiplier tubes (PMTs), due to their sensitivity (individual photon counting) and relatively high quantum efficiency (~40%). Because PMTs saturate easily, the microscope is typically light-shielded, and imaging performed in a dark room. However, these detectors are not wavelength sensitive, and require optics to select the correct color for detection. In a two-channel microscope, a secondary long-pass dichroic divides the fluorescent emission light into two color channels, and a glass filter placed before the PMT has a bandpass matching the fluorescent emission profile of the fluorophore of interest. Dichroics and filters are chosen to independently detect each color as much as possible, and avoid light leakage between the channels for clear color discrimination. Other channel optics such as lenses collect the fluorescence from the objective and focus the fluorescence on the relatively small active area of the PMT. As every photon contributes to signal, high efficiency is critical in the design of detection optics.

In a system using PMTs as optical detectors, PMTs provide a low level current output, which is converted to a voltage and amplified using a preamplifier circuit. High frequency noise is often filtered with a lowpass filter, set to a cutoff frequency inversely proportional to the amount of time the laser spends per pixel (the pixel dwell time). Data acquisition boards are typically used to generate signals to control the scan mirrors, laser power, laser shutters, and acquire analog PMT signals. Software may be used to orchestrate these settings while providing real-time visualization of the acquired images and controlling sample motion.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Only a few implementations and examples are described and other implementations, enhancements and variations can be made based on what is described and illustrated in this patent document.

What is claimed is what is described and illustrated, including:

1. A microscope, comprising:
   a sample stage that holds a sample to be imaged, wherein the sample includes overlapping fluorescent labels;

a light source that generates different excitation beams at different excitation wavelengths that interact with fluorescently-labeled structures within the sample to cause nonlinear optical absorption of two or more photons at each excitation wavelength and leading to fluorescent emission of light at one or more fluorescent emission wavelengths different from the corresponding excitation wavelength;
an optical input device located in optical paths of the excitation beams between the light source and the sample stage and structured to direct the excitation beams to the sample stage;
a microscope objective located in optical paths of the excitation beams between the optical input device and the sample stage to direct the excitation beams toward the sample stage to illuminate the sample and to collect light from the sample;
an optical output device located relative to the microscope objective to receive collected light by the microscope objective from the sample and select emitted fluorescent light at the fluorescent emission wavelengths as an output beam while excluding from the output beam light at each excitation wavelength, wherein the optical output device includes wavelength-selective optical devices that separate the output beam into a plurality of broad optical channel output beams along a plurality of optical channel optical paths at a plurality of designated fluorescent imaging wavelength bands, respectively, one optical channel output beam from one wavelength-selective optical device;
optical channel detectors located along the different optical channel optical paths to receive the different optical channel output beams, respectively, so that each optical channel detector receives a corresponding optical channel output beam and produces an optical channel detector output having information of the sample at within a corresponding fluorescent imaging wavelength band for the corresponding optical channel output beam; and
tunable optical channel filters including angle-tunable bandpass filters located between the optical channel detectors and wavelength-selective optical devices in the different optical channel optical paths, respectively, to receive the different optical channel output beams at the different designated fluorescent imaging wavelength bands, each tunable optical channel filter operable to spectrally tune by tuning angles of the angle-tunable bandpass filters and select light at different fluorescent imaging wavelengths within a corresponding designated fluorescent imaging wavelength band to be present in a corresponding optical channel output beam to be received by a corresponding optical channel detector, wherein each optical channel output beam from an optical channel detector contains imaging information at the different fluorescent imaging wavelengths within a corresponding designated fluorescent imaging wavelength band and the different optical channel output beams contain imaging information at the different fluorescent imaging wavelengths in the designated fluorescent imaging wavelength bands, wherein each tunable optical channel filter separates each broad optical channel output beam into a plurality of successive fluorescent images to obtain a plurality of distinct wavelength images per each broad optical channel from the overlapping fluorescent labels,
wherein the microscope is configured to alternate combinations of the excitation wavelength of the light source and the angles of the angle-tunable bandpass filters.

2. The microscope as in claim 1, wherein the optical input device includes one or more scan mirrors and one or more dichroic mirrors.

3. The microscope as in claim 1, wherein the light source includes a plurality of excitation beam generators, each excitation beam generator produces different excitation beam with different color from each other.

4. The microscope as in claim 1, wherein the light source generates a rapidly-tunable laser tuned to multiple consecutive wavelengths.

5. The microscope as in claim 1, wherein the light source further includes a power control system and a shutter configured to tune the excitation beams to a predetermined wavelength span.

6. The microscope as in claim 1, further comprising a path selector configured to select one path between a path from the light source to the microscope objective and a path from the microscope objective to the channel divider.

7. The microscope as in claim 6, wherein the path selector includes a dichroic mirror that allows the excitation beam to pass therethrough and to deflect the light emitted by the sample to the optical output device.

8. The microscope as in claim 1, further comprising a beam scanner that is placed between the optical input device and the microscope objective and is configured to redirect the excitation beam for sample scanning purposes.

9. The microscope as in claim 1, further comprising a lens system placed after the scan mirror and before the microscope objective to translate a beam angle of the excitation light into a position in the field of view of the microscope objective.

10. The microscope as in claim 1, wherein the optical output device includes a plurality of dichroic mirrors.

11. The microscope as in claim 1, further comprising a stage positioner that moves the sample stage relative to a focus of the excitation beam.

12. The microscope as in claim 1, wherein each optical channel optical path includes one or more condensing lenses and a photomultiplier tube after each tunable optical channel filter to focus an emission spectrum onto the photomultiplier tube and translate the emission spectrum at the photomultiplier tube.

13. The microscope as in claim 1, wherein the optical emission output device collects a divergent cone of light from a back aperture of the microscope objective, and retains a signal from scattered photons from the sample.

14. A method of microscopy based on multiphoton excitation, comprising:
generating different excitation laser wavelengths of excitation light for multiphoton excitation with respect to certain fluorescent labeling tags used in a sample;
sequentially directing excitation laser beams at the different selected excitation laser wavelengths to the sample to cause emission of fluorescent light in a florescent spectrum due to nonlinear multiphoton excitation at each excitation laser wavelengths;
collecting the fluorescent light emitted from the sample at a corresponding fluorescent spectrum associated with each of the different excitation laser wavelengths;
dividing collected light in each fluorescent spectrum into different broad color channels;
using angle-tunable bandpass filters to select, by tuning angles of angle-tunable bandpass filters, different imaging wavelengths within each broad color channel to be imaged to obtain images at different fluorescent imaging wavelengths within each and all broad color channels;

alternating combinations of the excitation laser wavelength of the excitation light and the angles of the angle-tunable bandpass filters; and processing obtained images at different fluorescent imaging wavelengths within each and all broad color channels to extract information on the sample.

15. The method as in claim 14, further comprising directing the multiple excitation laser beams along a common optical path to the sample.

16. The method as in claim 14, wherein selecting different excitation laser wavelengths of excitation light includes alternating excitation light sources.

17. The method as in claim 16, further comprising adjusting the positions of angle-tunable bandpass filters on a frame-by-frame basis.

18. The method as in claim 14, further comprising performing a calibration to compensate for differences in a photomultiplier tube gain by imaging a calibration light source and calculated appropriate image scaling factors for the photomultiplier tube gain settings.

19. A method of imaging a sample based on nonlinear optical absorption and emission in the sample, comprising:

directing to a sample including overlapping fluorescent labels different excitation beams at different excitation wavelengths that interact with the sample to cause nonlinear optical absorption of two or more photos at each excitation wavelength to emit fluorescent light at one or more fluorescent emission wavelengths different from the corresponding excitation wavelength;

operating a microscope objective to direct the excitation beams toward the sample to illuminate the sample and to collect light from the sample, wherein the collected light at the microscope objective includes returned excitation light at the excitation wavelengths and emitted fluorescent light via nonlinear optical absorption at fluorescent emission wavelengths;

selecting from the collected light by the microscope objective from the sample the emitted light at the fluorescent emission wavelengths by the sample as an output beam;

separating the output beam into a plurality of broad optical channel output beams along a plurality of optical channel optical paths at a plurality of designated fluorescent imaging wavelength bands, respectively;

operating angle-tunable bandpass filters to tune angles of the angle-tunable bandpass filters in the plurality of optical channel optical paths, respectively, to receive and filter the plurality of optical channel output beams at the plurality of designated fluorescent imaging wavelength bands so that each optical channel filter selects light at different fluorescent imaging wavelengths within a corresponding designated fluorescent imaging wavelength band to be in a corresponding optical channel output beam while collecting all available light at each fluorescent imaging wavelength within a corresponding designated fluorescent imaging wavelength band in the corresponding optical channel output beam without using an optically dispersive element to spatially separate light at different fluorescent imaging wavelengths within each corresponding designated fluorescent imaging wavelength band, wherein each optical channel filter separates each broad optical channel output beam into a plurality of successive fluorescent images to obtain a plurality of distinct wavelength images per each broad optical channel from the overlapping fluorescent labels;

operating different optical channel detectors located along the different optical channel optical paths to receive the different optical channel output beams, respectively, so that each optical channel detector receives a corresponding optical channel output beam at the different fluorescent imaging wavelengths for each and all designated fluorescent imaging wavelength bands and produces optical channel detector outputs having information of the sample at the different fluorescent imaging wavelengths for each and all designated fluorescent imaging wavelength bands; and alternating combinations of the excitation wavelength of the light source and the angles of the angle-tunable bandpass filters to acquire hyperspectral images.

20. The method as in claim 19, wherein each optical channel filter includes an angle tunable bandpass filter which changes a bandpass transmission wavelength with an angle of the angle tunable bandpass filter.

21. The method as in claim 19, further comprising:

scanning each excitation beam relative to the sample to illuminate different parts of the sample for extracting information on the different parts of the sample.

* * * * *

UNITED STATES PATENT AND TRADEMARK OFFICE
CERTIFICATE OF CORRECTION

| | |
|---|---|
| PATENT NO. | : 10,394,008 B2 |
| APPLICATION NO. | : 15/788778 |
| DATED | : August 27, 2019 |
| INVENTOR(S) | : Amanda J. Bares et al. |

Page 1 of 1

It is certified that error appears in the above-identified patent and that said Letters Patent is hereby corrected as shown below:

In the Specification

Column 1, after Line 14, please add the following new section header and new paragraph:
-- STATEMENT REGARDING FEDERALLY SPONSORED RESEARCH OR DEVELOPMENT
This invention was made with government support under grant number W81XWH-16-1-0666 awarded by the U.S. Army Medical Research Acquisition Activity Office of the Department of Defense. The government has certain rights in the invention. The government has certain rights in the invention. --

Signed and Sealed this
Twenty-third Day of May, 2023

Katherine Kelly Vidal
*Director of the United States Patent and Trademark Office*